(12) United States Patent
Bogdanovich

(10) Patent No.: US 10,432,257 B2
(45) Date of Patent: *Oct. 1, 2019

(54) METHODS, SYSTEMS, AND APPARATUS FOR THE MONITORING, CONTROLLING, AND COMMUNICATING OF ELECTRONIC DEVICES

(71) Applicant: Crius Technology Group, LLC, Austin, TX (US)

(72) Inventor: Phillip Bogdanovich, Austin, TX (US)

(73) Assignee: Crius Technology Group, LLC, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/783,833

(22) Filed: Oct. 13, 2017

(65) Prior Publication Data

US 2018/0102809 A1 Apr. 12, 2018

Related U.S. Application Data

(63) Continuation of application No. 15/404,174, filed on Jan. 11, 2017, now Pat. No. 9,793,952, which is a
(Continued)

(51) Int. Cl.
*H04B 3/00* (2006.01)
*H04L 25/00* (2006.01)
(Continued)

(52) U.S. Cl.
CPC ............... *H04B 3/54* (2013.01); *H04B 3/56* (2013.01); *H04L 12/2816* (2013.01);
(Continued)

(58) Field of Classification Search
CPC ........ H04B 3/54; H04B 3/56; H05B 37/0263; H05B 37/0272; H04L 12/40;
(Continued)

(56) References Cited

U.S. PATENT DOCUMENTS 7,853,809 B2   12/2010   Zhang et al.
9,793,952 B1 *   10/2017   Bogdanovich ........... H04B 3/54
(Continued)

OTHER PUBLICATIONS

Non-final Office Action, U.S. Appl. No. 15/404,174 dated Mar. 10, 2017, 20 pages.
(Continued)

*Primary Examiner* — Phuong Phu
(74) *Attorney, Agent, or Firm* — Akerman LLP; Mammen P. Zachariah, Jr.

(57) ABSTRACT

Methods, systems, and apparatus for monitoring and controlling electronic devices using wired and wireless protocols are disclosed. The systems and apparatus may monitor their environment for signals from electronic devices. The systems and apparatus may take and disambiguate the signals that are received from the devices in their environment to identify the devices and associate control signals with the devices. The systems and apparatus may use communication means to send control signals to the identified electronic devices. Multiple apparatuses or systems may be connected together into networks, including mesh networks, to make for a more robust architecture.

9 Claims, 12 Drawing Sheets

Related U.S. Application Data continuation-in-part of application No. 14/806,531, filed on Jul. 22, 2015, now abandoned.

(60) Provisional application No. 62/027,626, filed on Jul. 22, 2014, provisional application No. 62/027,627, filed on Jul. 22, 2014.

(51) Int. Cl.
| | |
|---|---|
| *H04B 3/54* | (2006.01) |
| *H05B 37/02* | (2006.01) |
| *H04W 4/80* | (2018.01) |
| *H04L 12/24* | (2006.01) |
| *H04L 12/28* | (2006.01) |
| *H04L 12/26* | (2006.01) |
| *H04B 3/56* | (2006.01) |

(52) U.S. Cl.
CPC .......... *H04L 41/0833* (2013.01); *H04L 43/00* (2013.01); *H04W 4/80* (2018.02); *H05B 37/0227* (2013.01); *H05B 37/0263* (2013.01); *H05B 37/0272* (2013.01); *H04L 43/08* (2013.01); *H04L 2012/2843* (2013.01)

(58) Field of Classification Search
CPC ............. H04L 41/0833; H04L 12/2816; H04L 2012/2843; H04L 43/08; H04W 4/008; H04W 4/80

USPC .... 375/219, 220, 222, 257, 258; 307/18, 52; 455/402, 41.1, 41.2

See application file for complete search history.

(56) References Cited

U.S. PATENT DOCUMENTS

| | | | |
|---|---|---|---|
| 2010/0130142 A1* | 5/2010 | Schubert ................ | H01R 13/66 455/90.3 |
| 2011/0320434 A1 | 12/2011 | Carston et al. | |
| 2012/0173900 A1 | 7/2012 | Diab et al. | |
| 2013/0057158 A1 | 3/2013 | Josefowicz et al. | |
| 2013/0275174 A1 | 10/2013 | Bennett et al. | |
| 2014/0040160 A1 | 2/2014 | Comito | |
| 2014/0058577 A1 | 2/2014 | Erhart et al. | |
| 2014/0175875 A1* | 6/2014 | Newman, Jr. ........... | H04L 69/18 307/18 |

OTHER PUBLICATIONS

Non-final Office Action, U.S. Appl. No. 16/118,544 dated Feb. 15, 2019, 14 pages.
Non-final Office Action, U.S. Appl. No. 14/806,511 dated Sep. 1, 2017, 15 pages.
Final Office Action, U.S. Appl. No. 14/806,511 dated May 11, 2018, 16 pages.
Non-final Office Action, U.S. Appl. No. 14/600,466 dated Dec. 23, 2016, 20 pages.
Ex Parte Quayle Office Action, U.S. Appl. No. 16/118,550 dated Mar. 15, 2019, 9 pages.

\* cited by examiner

METHODS, SYSTEMS, AND APPARATUS FOR THE MONITORING, CONTROLLING, AND COMMUNICATING OF ELECTRONIC DEVICES

PRIORITY CLAIM

This patent application is a continuation of U.S. patent application Ser. No. 15/404,174 entitled "METHODS, SYSTEMS, AND APPARATUS FOR THE MONITORING, CONTROLLING, AND COMMUNICATING OF ELECTRONIC DEVICES" to Bogdanovich, filed Jan. 11, 2017, which is a continuation-in-part of U.S. patent application Ser. No. 14/806,531 entitled "METHODS, SYSTEMS, AND APPARATUS FOR THE MONITORING, CONTROLLING, AND COMMUNICATING OF LIGHTING SYSTEMS" to Bogdanovich, filed Jul. 22, 2015, which claims priority to U.S. Provisional Patent Application No. 62/027,627 to Bogdanovich, entitled "COMMUNICATION CUBE METHOD AND SYSTEM", filed Jul. 22, 2014 and U.S. Provisional Patent Application No. 62/027,626 to Bogdanovich, entitled "HALL-EFFECT ELECTRIC POWER MONITOR", filed Jul. 22, 2014, all of which are incorporated by reference in their entireties.

CROSS-REFERENCE TO RELATED APPLICATIONS

This application incorporates by reference U.S. patent application Ser. No. 14/806,511 filed Jul. 22, 2015 in its entirety.

BACKGROUND

The invention relates generally to the field of monitoring, controlling, and communicating of devices. More particularly, the invention relates to a radio communication to power line communication bridge and networking system for the monitoring, controlling, and communicating of devices such as lighting systems.

SUMMARY

In one respect, disclosed may be a method for monitoring, controlling, and communicating. The method may comprise: splicing at least one control clamp to the power lines of at least one device; establishing a powernet control unit (PCU) power line communication link between at least one powernet control unit; connecting at least one of the at least one powernet control unit to a communication gateway in order to enable communication with the powernet control unit from a mobile device, a local server, and/or a remote server using a powernet control unit/communication cube (PCU/CC) dashboard application; using a PCU inter-PCU/CC wireless module and a communication cube (CC) inter-PCU/CC wireless module to communicate between the at least one powernet control unit and at least one communication cubes; using CC inter-PCU/CC wireless modules to communicate between the at least one communication cube; using the PCU power line communication link to communicate with the at least one powernet control unit; using the at least one communication cube with the spliced at least one control clamp to monitor and control the at least one device; using RFID modules and Bluetooth modules of the at least one communication cube to create at least one RFID/Bluetooth beacon; and using at least one monitor sensor of the at least one communication cube to monitor the area around the at least one device.

In another respect, disclosed is a method for monitoring, controlling, and communicating. The method may comprise: splicing at least one control clamp to the power lines of at least one device; establishing a power line communication link between at least one powernet control communication cube; connecting at least one of the at least one powernet control communication cube to a communication gateway in order to enable communication with the at least one powernet control communication cube from at least one of a mobile device and a remote server using a powernet control communication cube (PCCC) dashboard application; using a communication port of the at least one powernet control communication cube to communicate between the at least one powernet control communication cube; using the power line communication link to communicate between the at least one powernet control communication cube; using the at least one powernet control communication cube with the spliced at least one control clamp to monitor and control the at least one device; using RFID modules and Bluetooth modules of the at least one powernet control communication cube to create at least one RFID/Bluetooth beacon; and using at least one monitor sensor of the at least one powernet control communication cube to monitor the area around the at least one device.

In one respect, disclosed is an apparatus for monitoring, controlling, and communicating. The apparatus may comprise: at least one powernet control unit, wherein the power control unit (PCU) may comprise: a PCU housing; a PCU system bus within the PCU housing; at least one PCU processor coupled to the PCU system bus; PCU system memory coupled to the at least one PCU processor; at least one PCU non-transitory memory unit coupled to the at least one PCU processor; a GPS module coupled to the PCU system bus; a power port coupled to the PCU system bus; a PCU internal battery coupled to the PCU system bus; a communication port coupled to the PCU system bus, wherein the communication port may comprise at least one of: Wi-Fi, Ethernet, and a cellular network radio; a PCU inter-PCU/CC wireless module coupled to the PCU system bus, wherein the PCU inter-PCU/CC wireless module may comprise at least one of: Bluetooth, 6LoWPan, and ZigBee; and PCU code stored on the at least one PCU non-transitory memory unit; a communication gateway coupled to the communication port, wherein the communication gateway may be connected to a cloud; at least one of a local server and a mobile device connected to the communication gateway and configured to communicate with the PCU through the communication gateway; at least one of a remote server and a mobile device connected to the cloud and configured to communicate with the PCU through the communication gateway; and at least one communication cube, wherein the communication cube (CC) may comprise: a CC housing; a CC system bus within the communication cube CC housing; at least one CC processor coupled to the CC system bus; CC system memory coupled to the at least one CC processor; at least one CC non-transitory memory unit coupled to the at least one CC processor; an RFID module coupled to the CC system bus; a Bluetooth module coupled to the CC system bus; a CC internal battery coupled to the CC system bus; a CC inter-PCU/CC wireless module coupled to the CC system bus, wherein the CC inter-PCU/CC wireless module may comprise at least one of: Bluetooth, 6LoWPan, and ZigBee; at least one control port coupled to the CC system bus; at least one control clamp coupled to the at least one control port; at least one monitor sensor coupled to the CC system bus; and CC code stored on the at least one CC non-transitory memory unit; wherein the PCU code when executed by the at least one PCU processors may be configured to perform a PCU method that may comprise: establishing a PCU power line communication link between the at least one powernet control unit; communicating with the at least one powernet control unit through the PCU power line communication link; communicating with the at least one communication cube through the PCU inter-PCU/CC wireless module and the CC inter-PCU/CC wireless module; and communicating with a PCU/CC dashboard application; and wherein the CC code when executed by the at least one CC processor may be configured to perform a CC method that may comprise: communicating with the at least one powernet control unit through the PCU inter-PCU/CC wireless module and the CC inter-PCU/CC wireless module; communicating with the at least one communication cube through the CC inter-PCU/CC wireless module; monitoring and controlling at least one device through the at least one control clamp, wherein the at least one device may comprise a lighting system; creating an RFID/Bluetooth beacon; and monitoring the at least one monitor sensor.

In another respect, disclosed may be an apparatus for monitoring, controlling, and communicating. The apparatus may comprise: at least one powernet control communication cube, wherein the powernet control communication cube (PCCC) may comprise: a housing; a system bus within the housing; at least one processor coupled to the system bus; system memory coupled to the at least one processor; at least one non-transitory memory unit coupled to the at least one processor; a GPS module coupled to the system bus; a power port coupled to the system bus; an internal battery coupled to the system bus; a communication port coupled to the system bus, wherein the communication port may comprise at least one of: Wi-Fi, PLC, Ethernet, ZigBee, 6LoWPan, and Bluetooth; at least one control port coupled to the system bus; at least one control clamp coupled to the at least one control port; at least one monitor sensor coupled to the system bus; and PCCC code stored on the at least one non-transitory memory unit; a communication gateway coupled to the communication port, wherein the communication gateway may be connected to a cloud; at least one of a local server and a mobile device connected to the communication gateway and configured to communicate with the PCCC through the communication gateway; and at least one of a remote server and a mobile device connected to the cloud and configured to communicate with the PCCC through the communication gateway; wherein the PCCC code when executed by the at least one processor may be configured to perform a PCCC method that may comprise: establishing a power line communication link between the at least one powernet control communication cube; communicating with a PCCC dashboard application; communicating with the at least one powernet control communication cube through the power line communication link; communicating with the at least one powernet control communication cube through the communication port; monitoring and controlling at least one device through the at least one control clamp, wherein the at least one device may comprise a lighting system; creating an RFID/Bluetooth beacon; and monitoring the at least one monitor sensor.

Numerous additional embodiments may also be possible.

BRIEF DESCRIPTION OF THE DRAWINGS

Other objects and advantages of the invention may become apparent upon reading the detailed description and upon reference to the accompanying drawings.

Figure 1:
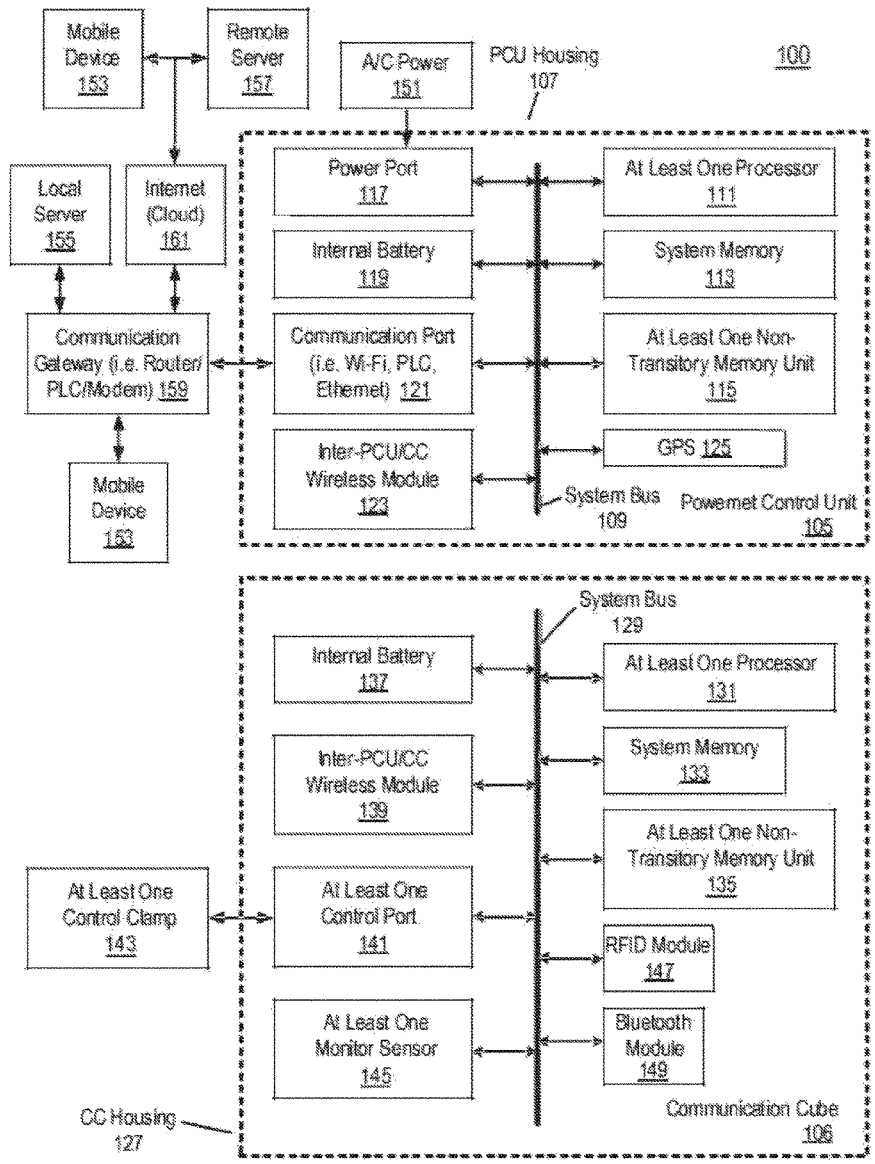
FIG. 1 is a block diagram illustrating an apparatus for monitoring, controlling, and communicating in accordance with embodiments.

While the invention is subject to various modifications and alternative forms, specific embodiments thereof are shown by way of example in the drawings and the accompanying detailed description. It should be understood, however, that the drawings and detailed description are not intended to limit the invention to the particular embodiments. This disclosure is instead intended to cover all modifications, equivalents, and alternatives falling within the scope of the present invention as defined by the appended claims.

DETAILED DESCRIPTION

One or more embodiments of the invention are described below. It should be noted that these and any other embodiments are exemplary and are intended to be illustrative of the invention rather than limiting. While the invention is widely applicable to different types of systems, it is impossible to include all of the possible embodiments and contexts of the invention in this disclosure. Upon reading this disclosure, many alternative embodiments of the present invention will be apparent to persons of ordinary skill in the art.

With the growth of the Internet of Things, existing devices are becoming networked in order to enable the monitoring, controlling, and communicating of the devices. Lighting and lighting systems are devices that are becoming networked in order to control power, color, and brightness. Currently, the method for incorporating a control system into an existing lighting system may be carried out by running wire or cable from a control device/panel to the lighting system. The running of the wire or cable may cost $10,000 per floor and may require days to accomplish. Additionally, the control device/panel may cost between $10,000 to $15,000. With such economics, the implementation of the Internet of Things to existing lighting systems has been slow in coming.

A method, apparatus, and system for monitoring, controlling, and communicating of devices may be described. The method, apparatus, and system may use a radio communication to power line communication bridge and networking system for the monitoring, controlling, and communicating of devices such as lighting systems. This method, apparatus, and system may not require the running of wire or cable and may be deployed in hours, not days, at a fraction of the cost of existing control systems. Since the apparatus may be used with any lighting fixture or lamp brand, the apparatus may be integrated into any existing lighting system.

FIG. 1 is a block diagram illustrating an apparatus for monitoring, controlling, and communicating in accordance with embodiments.

In embodiments, apparatus 100 may comprise at least one powernet control unit and at least one communication cube. The powernet control unit (PCU) 105 may comprise a PCU housing 107, a system bus 109, at least one processor 111, system memory 113, at least one non-transitory memory unit 115, a power port 117, an internal battery 119, a communication port 121, an inter-PCU/CC wireless module 123, and a GPS module 125, all of which may be directly or indirectly coupled to each other. The communication cube (CC) 106 may comprise a CC housing 127, a system bus 129, at least one processor 131, system memory 133, at least one non-transitory memory unit 135, an internal battery 137, an inter-PCU/CC wireless module 139, at least one control port 141, at least one control clamp 143, at least one monitor sensor 145, a RFID module 147, and a Bluetooth module 149, all of which may be directly or indirectly coupled to each other. In the installation of the apparatus, the PCU 105 may be mounted on the back of a flat electrical strike plate and may be powered by the internal battery 119 or by A/C power 151 through the power port 117 in embodiments. In embodiments, the communication port 121 may comprise at least one of a Wi-Fi radio, an Ethernet port, and a power line communication (PLC) bridge and may allow for the communication between powernet control units 105 and external control and monitoring devices such as mobile device 153, local server 155, and/or remote server 157. For Wi-Fi, PLC, and Ethernet, communication may be established through a communication gateway 159 such as a router/PLC/modem. Using a communication cube control web portal or a communication cube control app (PCU/CC dashboard application), at least one of the local server 155 and the mobile device 153 may be used to communicate with the PCU 105 and the CC 106 through the communication gateway 159. Additionally, the communication gateway 159 may be connected to the Internet 161, thus making it possible for the remote server 157 and/or the mobile device 153, using a communication cube control web portal or a communication cube control app, to communicate with the PCU 105 and the CC 106. The PCU 105 may communicate with the CC 106 through the inter-PCU/CC wireless module 123 of the PCU 105 with the inter-PCU/CC wireless module 139 of the CC 106. The inter-PCU/CC wireless modules 123, 139 may comprise at least one of a Bluetooth radio, 6LoWPan radio, and ZigBee radio. Bluetooth, 6LoWPan, and ZigBee may encompass all past, current, and future versions of the wireless protocols. The powernet control units which are connected to the PLC may be nodes which in turn may be in communication with the communication cubes 106. Each PCU node may be capable of identifying the communication cubes 106 which are connected to it. This network of communication cubes 106 connected to PCU nodes which are connected via PLC may be referred to as a powernet.

In embodiments, the CC 106 may be mounted within a lighting fixture and may be powered by the internal battery 137 or by one of the at least one control clamp 143 spliced into the power line to the lighting fixture. The control clamp may be designed to splice the power line to a lighting fixture without having to shut down power to the lighting fixture or device. After splicing the power line, direct power to the lighting fixture may be removed and the CC 106 may now be capable of controlling the lighting fixture or device, thus enabling control for dimming, color, and other primary and secondary functions such as, but not limited to Li-Fi management and emergency controls. Since the control clamp 143 is tapped into the power line, the control clamp 143 may also be able to provide power to the CC 106 through the control port 141. The CC 106 may also comprise at least one monitor sensor 145 to monitor for occupancy in the area of the lighting fixture as well as the lighting fixture location and status.

In embodiments, the RFID module 147 and Bluetooth module 149 of the CC 106 may be used to establish a beacon. The RFID module 147 may be used to monitor the space around the lighting fixture or device for any RFID transmitters. In a hospital setting, the RFID transmitters may be mounted onto tables, drug carts, wheel chairs, etc. The CC 106 may then be able to keep track of the RFID transmitters in the vicinity of the lighting fixture. The Bluetooth module 149 may be used to continuously ping the area around the lighting fixture for any nearby Bluetooth enabled devices. The vast majority of phones and devices since 2006 may respond to this pinging, thus enabling the CC 106 to map and monitor the number of people that are carrying Bluetooth phones and devices that are in the vicinity of the lighting fixture. The processing of the RFID and Bluetooth monitoring may be handled locally by the at least one processor 131 of the CC 106. By having this map of people and things, if a patient is looking for a particular facility within the hospital, the path of least resistance (i.e. least congestion) for the patient to get to the particular facility may be determined from the data collected from RFID monitoring and Bluetooth pinging. This path may be transmitted to the patient who is running the hospital's mobile application on a Bluetooth enabled phone. In embodiments, the Bluetooth module 149 may be used to transmit offers, promotions, or other information to an individual with a Bluetooth enabled phone running a particular store or promotion mobile application. In such a scenario, if a customer is shopping at a grocery store and is running a store's mobile application on a Bluetooth enabled phone and the customer approaches the soft drink aisle, the CC 106 may be able to determine that the customer is in the soft drink aisle and may be able to present the customer offers and promotions for products that are also in the soft drink aisle. The CC 106 may present offers for products that are available since the CC 106 may use its RFID module 147 to detect for products labeled with RFID tags.

Figure 2:
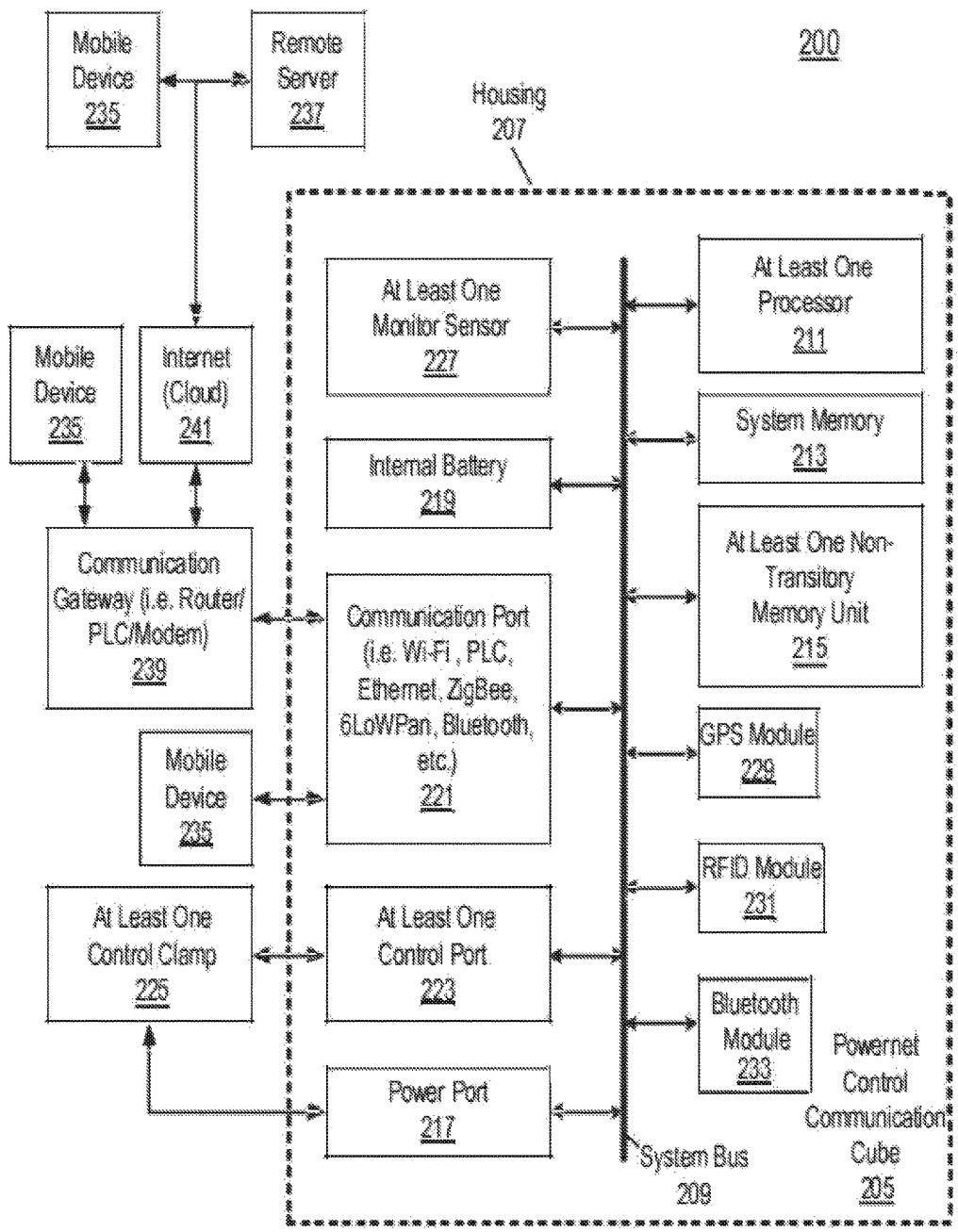
FIG. 2 is a block diagram illustrating an apparatus for monitoring, controlling, and communicating in accordance with embodiments.

FIG. 2 is a block diagram illustrating an apparatus for monitoring, controlling, and communicating in accordance with embodiments.

In embodiments, apparatus 200 may comprise at least one powernet control communication cube 205. The powernet control communication cube (PCCC) 205 may comprise a housing 207, a system bus 209, at least one processor 211, system memory 213, at least one non-transitory memory unit 215, a power port 217, an internal battery 219, a communication port 221, at least one control port 223, at least one control clamp 225, at least one monitor sensor 227, a GPS module 229, an RFID module 231, and a Bluetooth module 233, all of which may be directly or indirectly coupled to each other.

In embodiments, the PCCC 205 may be mounted within a lighting fixture or on the back of a flat electrical strike plate and may be powered by the internal battery 219 or by using one of the control clamps 225 coupled to the power port 217 to tap into a power line. Alternatively, the power port 217 may draw its power internally from one of the control clamps 225 connected to the control port 223. The communication port 221 may comprise at least one of a Wi-Fi radio, a PLC bridge, an Ethernet port, ZigBee radio, 6LoWPan radio, and a Bluetooth radio and may allow for the communication between powernet control communication cubes 205 and external control and monitoring devices such as mobile device 235 and remote server 237. Bluetooth, 6LoWPan, and ZigBee may encompass all past, current, and future versions of the wireless protocols. For Wi-Fi, PLC, and Ethernet, communication may be established through a communication gateway 239 such as a router/PLC/modem. Using a PCCC control web portal or a PCCC control app (PCCC dashboard application), the mobile device 235 may be used to communicate with the PCCC 205 through the communication gateway 239. Additionally, the communication gateway 239 may be connected to the Internet 241, thus making it possible for at least one of the remote server 237 and the mobile device 235, using a PCCC control web portal or a PCCC control app, to communicate with the PCCC 205. Using the Bluetooth radio of the communication port 221, the mobile device 235 may also be capable of communicating with the PCCC 205 through the communication port 221. The powernet control communication cubes 205 may also communicate with each other through the communication port 221 using the Bluetooth radio, 6LoWPan radio, and/or ZigBee radio. The powernet control communication cubes 205 which are connected to the PLC may be nodes which in turn may be in communication with the powernet control communication cubes 205 which may not be connected to the PLC. Each PCCC node may be capable of identifying the powernet control communication cubes 205 which may be connected to it. This network of powernet control communication cubes 205 connected to PCCC nodes which are connected via PLC may be referred to as a powernet. Lastly, the GPS module 229 may provide location data for the PCCC 205 and may allow for the traceability of the PCCC 205 in event of its theft.

In embodiments, the RFID module 231 and Bluetooth module 233 of the PCCC 205 may be used to establish a beacon. The RFID module 231 may be used to monitor the space around the lighting fixture or device for any RFID transmitters. In a hospital setting, the RFID transmitters may be mounted onto tables, drug carts, wheel chairs, etc. The PCCC 205 may then be able to keep track of the RFID transmitters in the vicinity of the lighting fixture. The Bluetooth module 233 may be used to continuously ping the area around the lighting fixture for any nearby Bluetooth enabled devices. The vast majority of phones and devices since 2006 will respond to this pinging, thus enabling the PCCC 205 to map and monitor the number of people that are carrying Bluetooth phones and devices that may be in the vicinity of the lighting fixture. The processing of the RFID and Bluetooth monitoring may be handled locally by the at least one processor 211 of the PCCC 205. By having this map of people and things, if a patient is looking for a particular facility within the hospital, the path of least resistance (i.e. least congestion) for the patient to get to the particular facility may be determined from the data collected from RFID monitoring and Bluetooth pinging. This path may be transmitted to the patient who is running the hospital's mobile application on a Bluetooth enabled phone. In embodiments, the Bluetooth 233 may be used to transmit offers, promotions, or other information to an individual with a Bluetooth enabled phone running a particular store or promotion mobile application. In such a scenario, if a customer is shopping at a grocery store and is running a store's mobile application on a Bluetooth enabled phone and the customer approaches the soft drink aisle, the PCCC 205 may be able to determine that the customer is in the soft drink aisle and may be able to present the customer offers and promotions for products that are also in the soft drink aisle. The PCCC 205 may present offers for products that are available since the PCCC 205 uses its RFID module 231 to detect for products labeled with RFID tags.

Figure 3:
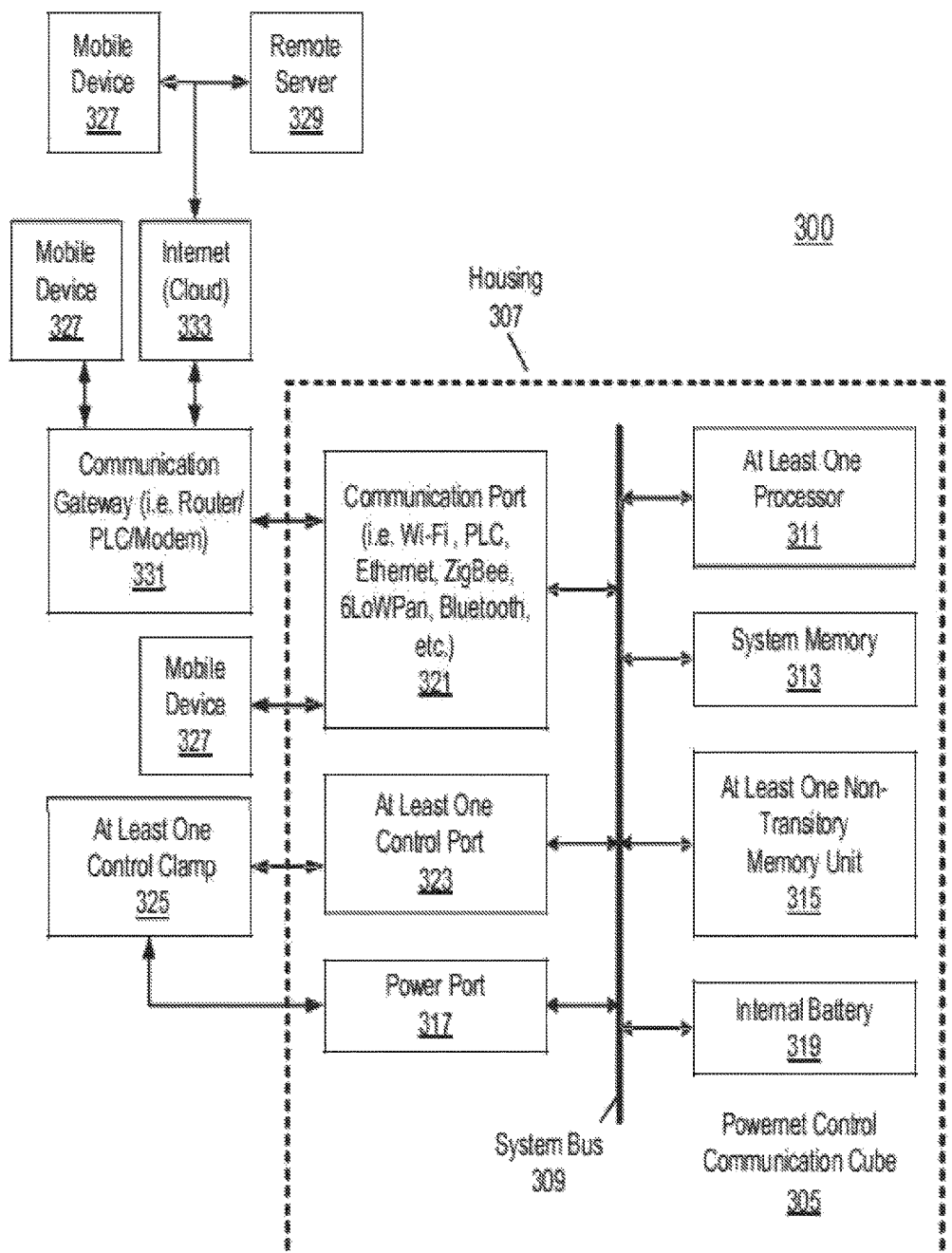
FIG. 3 is a block diagram illustrating an apparatus for monitoring, controlling, and communicating in accordance with embodiments.

FIG. 3 is a block diagram illustrating an apparatus for monitoring, controlling, and communicating in accordance with embodiments.

In embodiments, apparatus 300 may comprise at least one powernet control communication cube 305. The powernet control communication cube (PCCC) 305 may comprise a housing 307, a system bus 309, at least one processor 311, system memory 313, at least one non-transitory memory unit 315, a power port 317, an internal battery 319, a communication port 321, at least one control port 323, and at least one control clamp 325, all of which may be directly or indirectly coupled to each other.

In embodiments, the PCCC 305 may be mounted within a lighting fixture or on the back of a flat electrical strike plate and may be powered by the internal battery 319 or by using one of the control clamps 325 coupled to the power port 317 to tap into a power line. Alternatively, the power port 317 may draw its power internally from one of the control clamps 325 connected to the control port 323. The communication port 321 may comprise at least one of a Wi-Fi radio, a PLC bridge, an Ethernet port, ZigBee radio, 6LoWPan radio, and a Bluetooth radio and may allow for the communication between powernet control communication cubes 305 and external control and monitoring devices such as at least one of a mobile device 327 and a remote server 329. Bluetooth, 6LoWPan, and ZigBee may encompass all past, current, and future versions of the wireless protocols. For Wi-Fi, PLC, and Ethernet, communication may be established through a communication gateway 331 such as a router/PLC/modem. Using a PCCC control web portal or a PCCC control app (PCCC dashboard application), the mobile device 327 may be used to communicate with the PCCC 305 through the communication gateway 331. Additionally, the communication gateway 331 may be connected to the Internet 333, thus making it possible for at least one of the remote server 329 and the mobile device 327, using a PCCC control web portal or a PCCC control app, to communicate with the PCCC 305. Using the Bluetooth radio of the communication port 321, the mobile device 327 may also be capable of communicating with the PCCC 305 through the communication port 321. The powernet control communication cubes 305 may also communicate with each other through the communication port 321 using the Bluetooth radio, 6LoWPan radio, and/or ZigBee radio. The powernet control communication cubes 305 which may be connected to the PLC may be nodes which in turn may be in communication with the powernet control communication cubes which are not connected to the PLC. Each PCCC node may be capable of identifying the powernet control communication cubes 305 which may be connected to it. This network of powernet control communication cubes 305 connected to PCCC nodes which are connected via PLC may be referred to as a powernet.

In embodiments, the PCCC 305 may be used to control a single lamp, a single fixture, and/or a series of fixtures. For such an embodiment, the PCCC 305 may be mounted within the lighting fixture and may be powered by the internal battery 319 or by one of the at least one control clamp 325 spliced into the power line to the lighting fixture. The control clamp 325 may be designed to splice the power line to a lighting fixture without having to shut down power to the lighting fixture or device. After splicing the power line, direct power to the lighting fixture may be removed and the PCCC 305 may now be capable of controlling the lighting fixture, thus enabling control for dimming, color, and other primary and secondary functions such as, but not limited to Li-Fi management and emergency controls. Since the control clamp is tapped into the power line, the control clamp may also be able to provide power to the PCCC 305 through the power port 317. This embodiment was similarly disclosed in FIG. 2, except that in this embodiment, the components not required for controlling a lighting system, (the at least one monitor sensor, the GPS, the RFID, and Bluetooth) have been eliminated.

In embodiments, the components for communication through the communication gateway may be separated from the components for communication between the powernet control communication cubes 305. In such an embodiment, the powernet control unit may comprise at least one of the Wi-Fi radio, the Ethernet port, and the power line communication (PLC) bridge and the communication cube 305 may comprise at least one of a Bluetooth radio, 6LoWPan radio, and ZigBee radio, as was similarly disclosed in FIG. 1, except that in this embodiment, the components not required for controlling a lighting system (the at least one monitor sensor, the GPS, the RFID, and Bluetooth) have been eliminated.

Figure 4:
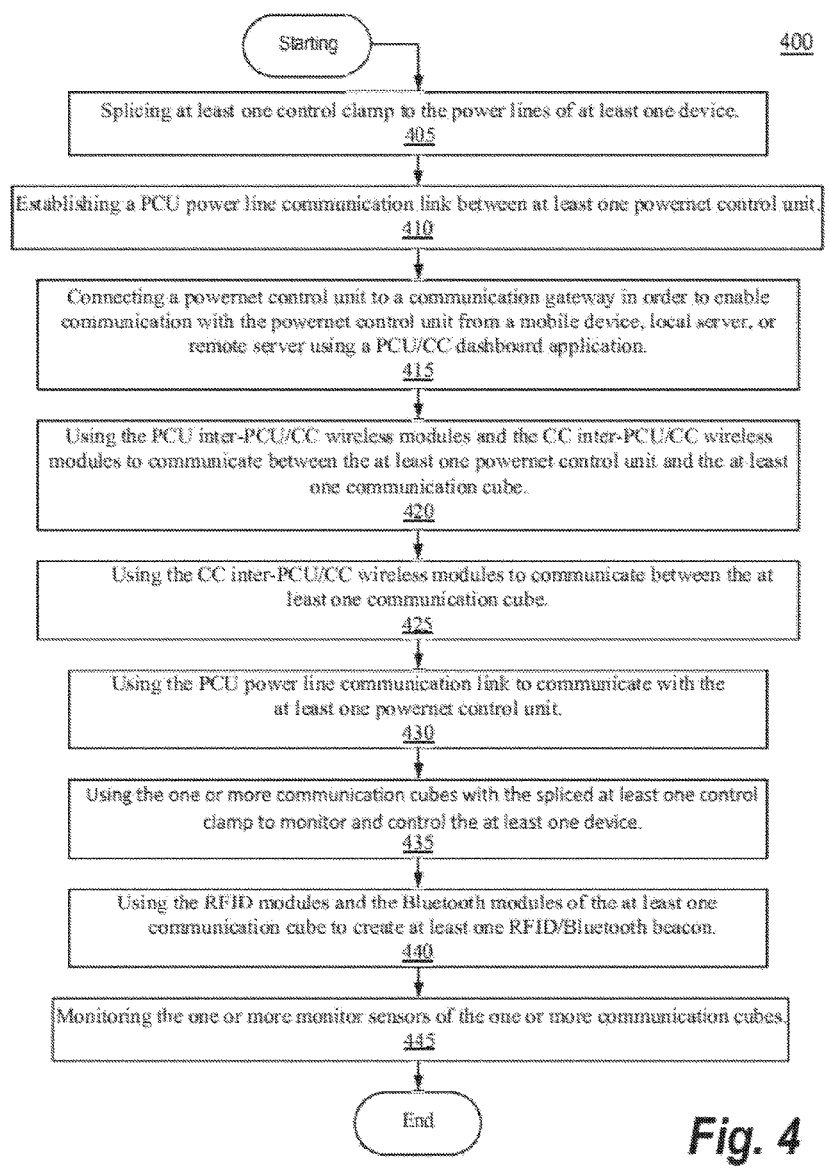
FIG. 4 is a block diagram illustrating a method for monitoring, controlling, and communicating of devices in accordance with embodiments.

FIG. 4 is a block diagram illustrating a method for monitoring, controlling, and communicating of devices in accordance with embodiments.

In embodiments, PCU code and CC code may be stored on the at least one PCU non-transitory memory unit and the at least one CC non-transitory memory unit, respectively, and executed by the at least one PCU processor and by the at least one CC processor, respectively, to perform a method 400 for monitoring, controlling, and communicating of devices. The method 400 illustrated in FIG. 4 may be performed by the apparatus illustrated in FIG. 1. Processing may begin in method 400 at block 405, wherein at least one control clamp may be spliced to the power lines of at least one device.

At block 410, a PCU power line communication link may be established for communication between at least one powernet control unit in embodiments.

At block 415, a powernet control unit may be connected to a communication gateway in order to enable communication with the powernet control unit from a mobile device, local server, or remote server using a PCU/CC dashboard application in embodiments.

At block 420, the PCU inter-PCU/CC wireless modules and the CC inter-PCU/CC wireless modules may be used to communicate between the at least one powernet control unit and the at least one communication cube in embodiments.

At block 425, the CC inter-PCU/CC wireless modules may be used to communicate between the at least one communication cubes in embodiments.

At block 430, the PCU power line communication link may be used to communicate with the at least one powernet control unit in embodiments.

At block 435, the at least one communication cube with the spliced at least one control clamp may be used to monitor and control the at least one device in embodiments.

At block 440, the RFID modules and the Bluetooth modules of the at least one communication cube may be used to create at least one RFID/Bluetooth beacon in embodiments.

At block 445, the at least one monitor sensor of the at least one communication cube may be monitored in embodiments. The at least one monitor sensor may be used to monitor for occupancy in the area of the device as well as the device location and status. Processing may subsequently end after block 445 in embodiments.

Figure 5:
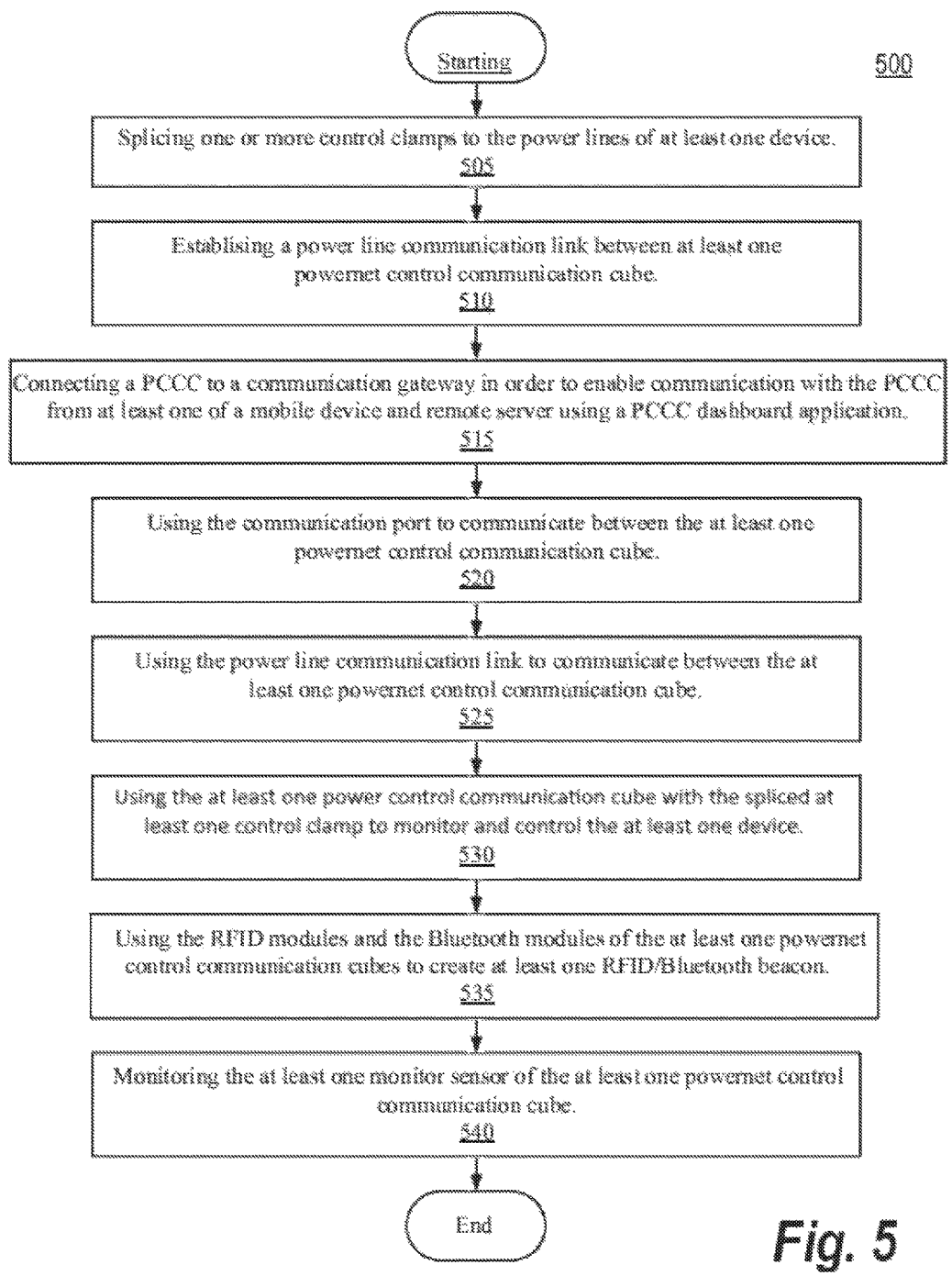
FIG. 5 is a block diagram illustrating a method for monitoring, controlling, and communicating of devices in accordance with embodiments.

FIG. 5 is a block diagram illustrating a method for monitoring, controlling, and communicating of devices in accordance with embodiments.

In embodiments, PCCC code may be stored on the at least one non-transitory memory unit and may be executed by the at least one processor to perform a method 500 for monitoring, controlling, and communication of devices. The method 500 illustrated in FIG. 5 may be performed by the apparatuses illustrated in FIG. 2 and FIG. 3. Processing may begin in method 500 at block 505, wherein at least one control clamp may be spliced to the power lines of at least one device.

At block 510, a power line communication link may be established for communication between at least one powernet control communication cube in embodiments.

At block 515, a PCCC may be connected to a communication gateway in order to enable communication with the PCCC from a mobile device and/or remote server using a PCCC dashboard application in embodiments.

At block 520, the communication port may be used to communicate between the at least one powernet control communication cube in embodiments.

At block 525, the power line communication link may be used to communicate between the at least one powernet control communication cube in embodiments.

At block 530, the at least one powernet control communication cube with the spliced at least one control clamp may be used to monitor and control the at least one device in embodiments.

At block 535, the RFID modules and the Bluetooth modules of the at least one powernet control communication cube may be used to create at least one RFID/Bluetooth beacon in embodiments.

At block 540, the at least one monitor sensor of the at least one powernet control communication cube may be monitored. The at least one monitor sensor may be used to monitor for occupancy in the area of the device as well as the device location and status. Processing may subsequently end after block 540 in embodiments.

Embodiments described herein relate to a computer storage product with at least one non-transitory memory unit having instructions or computer code thereon for performing various computer-implemented operations. The at least one memory unit are non-transitory in the sense that they do not include transitory propagating signals per se (e.g., a propagating electromagnetic wave carrying information on a transmission medium such as space or a cable). The at least one memory unit and computer code (also can be referred to as code) may be those designed and constructed for the specific purpose or purposes. Examples of at least one memory unit include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using Java, C++, Python, C, or other programming languages (e.g., object-oriented programming languages) and development tools. Additional examples of computer code include, but are not limited to, control signals, encrypted code, database code, and compressed code.

As discussed, a single multifunction communications cube (MCC) may have multiple means or subsystems for receiving and transmitting digital information. It will be understood that a multifunction communication cube (MCC) may include all, or a subset, of the same or similar components, features, and functionality of apparatus TOO, apparatus 200, and apparatus 300 described in detail elsewhere in this application. The MCC may use its communications subsystems or inputs (Wi-Fi, ZigBee, Bluetooth, PCL, Ethernet, etc.) to generate a "digital impression" or "digital profile" including digital impression information of the devices in its environment. The digital impression may contain essentially all, or a subset of, signal information across all of the CC's detection means for each and every device that the MCC can detect. The digital impression information collected about different devices in the environment of the MCC may differ in relation to signal information available and collected by the CC. The MCC may monitor all of the inputs simultaneously, or in any suitable order to generate such a digital impression. Monitoring of inputs by the MCC may include monitoring all or a subset of communications subsystems of the CC. This digital impression may be limited only by the inherent limitations of the different input methodologies or input subsystems of the CC. In an embodiment, for example, the CC's ability to monitor devices via its PLC inputs may be limited to devices connected to an electrical circuit accessible to the CC, while the devices observable via the CC's Bluetooth and Wi-Fi inputs may be limited to the communication reception ranges determined by each device's Bluetooth antenna range and Wi-Fi antenna range. The signal information from all inputs available to the MCC may be aggregated to generate the digital impression. Multiple CCs with overlapping sensor ranges may have separate digital impressions that contain devices that overlap, or alternatively, may be aggregated together to create a single, more thorough or complete digital impression of the devices around the plurality of networked CCs. In an embodiment, for example, a first MCC and second MCC in communication, directly or indirectly via other intermediate CC's relaying communications information between the first MCC and second CC, may have combined, coordinated, or cooperative capability to identify, monitor, and interact with devices via PLC inputs connected to any electrical circuit accessible or connected to either the first MCC and the second CC, and further may have combined, coordinated or cooperative capability to identify, monitor and interact with the same or other devices via Bluetooth and Wi-Fi inputs within wireless communication range of both the first MCC and second CC. In such an embodiment, for example, digital impressions of each of a plurality of devices may include digital impression information obtained via PLC inputs, Bluetooth inputs, and Wi-Fi inputs, of each and every device observable, directly or indirectly, by the first MCC and second CC.

In an exemplary scenario, if a MCC is installed into a powerline circuit in a room with a Wi-Fi enabled smart TV that is connected to the same powerline circuit as the CC, a Bluetooth and Wi-Fi enabled cell phone sitting by itself on a desk in the next room over, and a ZigBee enabled smoke detector connected to a separate powerline circuit in the hall between the two rooms, the MCC may receive both a PLC signal and a Wi-Fi signal from the TV, both Wi-Fi and Bluetooth signals from the cell phone, and a ZigBee signal from the smoke detector. The digital impression generated by the MCC would comprise all of these signals together.

The CC's onboard processor may aggregate this sensor data in order to generate the digital impression of the CC's environment. The MCC may then use its processor and information contained on its onboard memory to identify digital signatures of the different devices constituting the digital impression. If the digital impression cannot be disambiguated to determine the unique signatures identifying the constituent devices, the MCC may use one or more of its communications pathways to transmit the digital impression to a remote server, which may have access to more data and processing capabilities than the CC's onboard hardware in order to disambiguate the digital impression and determine what devices are being sensed by the CC. Once the digital impression has been disambiguated and the unique devices sensed by the MCC are identified that information along with control information for those devices may be communicated from the remote server back to the MCC through a suitable communication network. The unique device information may comprise information such as the make and model of the device, and may further comprise control information including, but not limited to control signals compatible with the identified device through one or more communications means, and a hierarchy of what communications means are preferred for controlling said device. Whether or not the MCC can determine the devices constituting the digital impression through onboard processing versus offboard processing at a remote server may be a question of the CC's form factor and current hardware limitations.

Once the MCC has either determined the identity of the devices that it sensed in its digital impression, or has received such information from the remote server, the MCC may then use any of the output methods available to it to communicate with and control the unique devices whose signals were include in the CC's digital impression. The determination of what communication means should be used to control which unique device may be associated with the information used to identify of the unique devices, and may be determined when the unique devices are identified. This control and control preference information may be stored either on the CC's or on the remote server's memory. This selection of the means by which to control the devices may be limited to the manner in which the MCC can communicate with that particular device (it would not be helpful for the MCC to try to control a Wi-Fi enabled TV via Wi-Fi if either the MCC does not possess Wi-Fi functionality, or if the MCC is in only powerline communication with the TV).

Continuing with the example provided above, once the MCC has formed a digital impression of its environment, including the PLC signature of the TV, the Wi-Fi signatures of the TV and the smartphone, the Bluetooth signature of the smartphone, and the ZigBee signature of the smoke detector, it may transmit this impression to a remote server, and receive back from the server information indicating the three devices and their control preferences. The stored device information indicates that the TV may be controlled via PLC, infra-red (IR), and Wi-Fi, but prefers to be controlled via IR or Wi-Fi; the smartphone prefers to be controlled by Bluetooth rather than Wi-Fi; and the smoke detector can be controlled by PLC or ZigBee and has no preference on which is better. In such a case, the MCC would control the TV via Wi-Fi as it is preferred over PLC and the MCC does not possess IR; the smartphone via Bluetooth as it is preferred over PLC; and the smoke detector via ZigBee as it is the only connection that the MCC has to that device.

In embodiments, the MCC may be limited to having fewer than all of the possible input and communications means. For example, one MCC may be configured for Ethernet and PLC communication only, while another MCC may be configured for Ethernet and Bluetooth communication only, while yet another MCC may be configured for wireless, Bluetooth, and PLC communication. Any permutation or combination of communication means may be provided for on any specific MCC without departing from the scope of this disclosure. Embodiments without the capability of at least one communications means may be termed a "limited CC". Multiple differently limited CCs, for example one that is limited to Bluetooth and PLC, and one limited to Bluetooth and Wi-Fi, may communicate together via their shared communication protocol. In such an example the Bluetooth and PLC limited MCC may relay its digital impression to a remote server by using its shared communication protocol (in this case Bluetooth) to relay information to the other CC, which may then transmit both its digital impression and the digital impression received from the other limited MCC to the remote server via Wi-Fi.

In embodiments, a single MCC may be configured to use any and all suitable communications means.

Multiple CCs may be networked together via suitable communications networks. Multiple CCs in a particular physical location may be considered a "node". Multiple nodes may be connected together to form a network or MCC network. In embodiments, a single node may constitute a network or MCC network.

The CCs in a node may transmit and receive communications with one another in order to determine which of the CCs has the strongest connection to a communication network capable of transmitting information to a target device external to the node. The other CCs of the node may then relay information to the target device through the MCC with said strongest connection. The MCC through which the node's information is relayed may update in the event that the connection strength changes. This may allow all of the CCs in the node to be able to communication with the remoted device even if any particular MCC cannot directly communicate with said remote device. Furthermore, this relaying of information between networked CCs does not have to be direct, and may be indirect. For example, a first MCC may transmit information to a second CC, which may in turn transmit the information from the first MCC to a third CC, that may then transmit the information from the first MCC to a remote device. This ability to relay information through a series of networked CCs may also provide for a "gap jumping" ability, where a MCC that is not capable of transmitting directly to a remote device may relay information through one or a series of connected CCs until one of them is able to establish a connection to the remote device.

This relaying of information between networked CCs does not have to be direct, and may be indirect. In embodiments, a plurality of CCs constituting a node may be connected together in a mesh network configuration. Such a mesh network of CCs, for example, may relay information using either a flooding technique or a routing technique. To ensure all its paths' availability, the network may allow for continuous connections and should be able to reconfigure itself around broken paths, using self-healing algorithms. Self-healing allows a routing-based network to operate when a node breaks down or when a connection becomes unreliable. Utilizing such a mesh network configuration, a first MCC may transmit information to a second CC, which may in turn transmit the information from the first MCC to a third CC, that may then transmit the information from the first MCC to a remote device. This ability to relay information through a series of networked CCs may also provide for a "gap jumping" ability, where a MCC that is not capable of transmitting directly to a remote device may relay information through one or a series of connected CCs until one of them is able to establish a connection to the remote device.

In an embodiment, a plurality of CCs may cooperate to identify and share digital impression information regarding network routers and network security devices, such as network security packet sniffers, of a secured network for evading detection by the secured network routers and network security devices while identifying, monitoring, interacting with, and controlling devices on the secured network. The plurality of CCs may establish and communicate over a separate mesh communications network, or over any other network accessible to the plurality of CCs. In embodiments, where the plurality of CCs may have developed and shared, or may have received from a remote server, digital impression information regarding network routers and network security devices at an established or acceptable confidence level, one or more of the plurality of CCs may communicate over a separate mesh network established between the plurality of CCs, and/or may communicate over the secured network according to protocols that are unidentifiable or undetectable by the secured network routers and network security devices so as to remain "dark" and undetected. In embodiments, one or more of the plurality of CCs may also communicate over the secured network according to protocols that are compatible, identifiable, or detectable by the secured network routers and network security devices so as to spoof or simulate other devices known to be on the network, or that might belong on the network, to misinform the secured network routers and network security devices regarding the security or unsecured status of the secured network, and/or also to misinform network security devices regarding operations and operating status of devices identifiable, or known, by the CCs. It will be understood that the term "devices" may include firmware and software associated with hardware devices or nodes.

In embodiments, CCs may automatically assign themselves identifiers. Automatic identification of the CCs may be performed, for example, in accordance with a 6LoPan protocol. A plurality of networked CCs may automatically share digital impression information for devices detectable by, or known to, any of the plurality of CCs, and automatically share instructions for monitoring, interacting with, and controlling such devices.

In an embodiment utilizing PLC monitoring and control of a device, the MCC may monitor the power line signals going through the circuit into which it is spliced. The MCC may also monitor wireless signals through a signal array including but not limited to WIFI, Bluetooth, RFID, ZigBee, and Specific Application Frequencies. The monitoring may be performed by the processor portion of the CC. The power line signals comprise waveforms that correspond to each of the electric devices on the circuit. Similarly, wireless devices can be identified by their respective MAC and IP address. A problem is presented that, because these signals are all running through the same power line, or through the same space in the instance of wireless signals, and into the same MCC device, the signals may become jumbled together or conflated, creating "signal noise". This signal noise on the PLC input to the MCC is a constituent part of the inputs that the MCC aggregates together to generate the digital impression. These individual signals within the digital impression and the signal noise must be disambiguated in order to identify the unique signals that are indicative of each unique device on the circuit. Signal strength and range are determined by a number of factors including but not limited to: whether there are physical barriers in between the transmitting and receiving devices, whether there is competing signal traffic, the relative strength of the signal being transmitted, the type of signal being transmitted, and the frequency the signal is being transmitted on.

In some embodiments, to disambiguate the unique device waveforms from signal noise of the PLC circuit, as well as the other signals picked up by the other input means or subsystems possessed by the MCC which constitute the digital impression, it is necessary to possess or access a database of signal waveforms and other unique device signatures and their associated devices. Such a database may comprise millions of unique signals each identifying a unique electrical device. For this reason, it may be impractical to maintain this database on the memory of a MCC itself Instead a remote device, such as a remote server, may be used to store the unique signal information and to do or perform the processing of the data needed to identify and disambiguate the constituent unique signals that comprise the signal noise or conflated signals. To provide the signal noise information from the MCC to the remote server, the MCC may record a portion of the single noise and transmit it, via suitable network connection, to the server. The server may run an algorithm to analyze the segment of signal noise received from the MCC to differentiate the individual signals from the signal noise. Once the individual signals have been identified, the server can match them to signals from the database of unique signals and identify their respective electrical devices. In an embodiment, a MCC or remote server may process signal noise or conflated signals to eliminate, adjust or compensate for signals of identified devices in the jumbled signal noise or conflated signals, and thus simplify or reduce processing steps and time required to identify remaining devices from their characteristic signals remaining in the adjusted or compensated signal noise or conflated signals.

Once the devices associated with the disambiguated signals have been identified by the server, the server can then transmit the identity of the electrical devices associated with the portion of signal noise transmitted to it back to the CC. Once the MCC has received the identity of the devices on its circuit from the server, it may then use signal commands for the associated devices to control the devices on its circuit. Unlike the unique signal identification information stored on the server, which can comprise massive amounts of information, signal commands may be compatible between related types of electronic devices and therefore require significantly smaller amounts of memory to store. Therefore, in some embodiments, the database of signal commands may be stored locally in the MCC in a local memory. Once the MCC has determined or received signal commands associated with the electric devices on its' circuit, the MCC can then use its processor to transmit waveforms corresponding to the signal commands associated with a particular device to control certain known characteristics of the particular device's operation.

In embodiments, the manner in which the MCC may be able to control the devices on its circuit vary depending on the device. For power modulation where there may no digital management capability. For example, for incandescent light bulb or older TVs, the only options will be off/on dim up/dim down. Those "commands" are managed through increasing or decreasing the voltage and/or current being transmitted to the device being controlled through the powerline. The MCC may effectuate such a modulation of voltage and/or current through the use of a series of circuits, or through a series of resistors/transistors if analog. For other devices, which may be controlled wirelessly, the MCC may provide control signals to the device through a suitable wireless communication means (e.g. Wi-Fi, Bluetooth, IR, etc.) rather than through modulation of the waveform of the power line into which the device is connected. For example, The MCC may identify a smart TV through the power line and identify it as a TV, and may then implement a control profile identified as usable via Wi-Fi or IR. The preference of control methodology for the specific device may associated with the unique device once it is identified. The preferred control means may be limited by the communications capabilities of the MCC that is trying to control the device.

Generally, not all electrical circuits in a building are connected. Even circuits within the same breaker panel are often not directly connected. Whether it is for meeting code requirements, load limit restrictions, security, redundancy, reduction of single point failure, or convenience, multiple distinct electrical circuits are used. Addressing these hurdles when implementing a network is an additional advantage of the MCC over current technologies. Multiple CC's can be networked together to create a mesh network spanning large open areas. Multiple CC's can also be connected to communicate along that circuit over great distances and through physical barriers like floors, walls, and ceilings. These CCs may be able to communicate with one another through alternate compatible communications means or subsystems if one such means of communication is not available. For example, if two CCs both have Wi-Fi functionality and are within Wi-Fi range of one another, but are not connected to the same powerline circuit, the two CC's may communicate through the Wi-Fi network (or indirectly through the MCC mesh network) rather than communicating via PLC. Since all CC's in proximity are able to communicate as programmed (meeting designated network security requirements), either wirelessly, wired, or both, a network of CC's can "jump" significant distances between electrical circuits, through physical barriers like floors and walls where wireless signals would not otherwise penetrate via powerline, or through electromagnetic barriers, via a wireless and/or wired mesh network. It will be understood that electromagnetic barriers may include, for example, a Faraday cage electromagnetic barrier.

Figure 11:
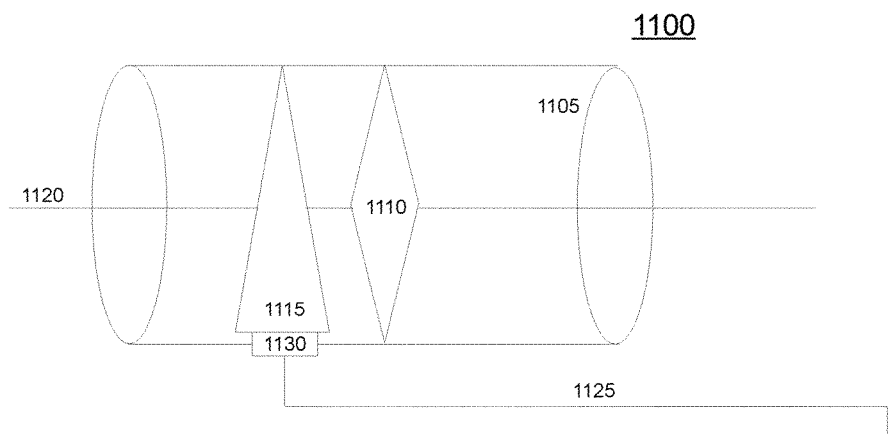
FIG. 11 illustrates aspects of a clamp for connecting a multifunction communication cube (MCC) to an electrical power circuit, in an embodiment.
Figure 12:
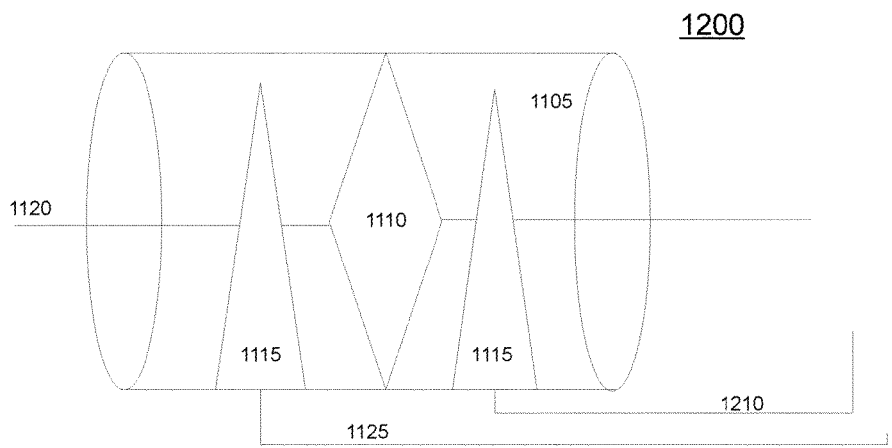
FIG. 12 illustrates aspects of a clamp for connecting a multifunction communication cube (MCC) to an electrical power circuit, in an embodiment.
Figure 13:
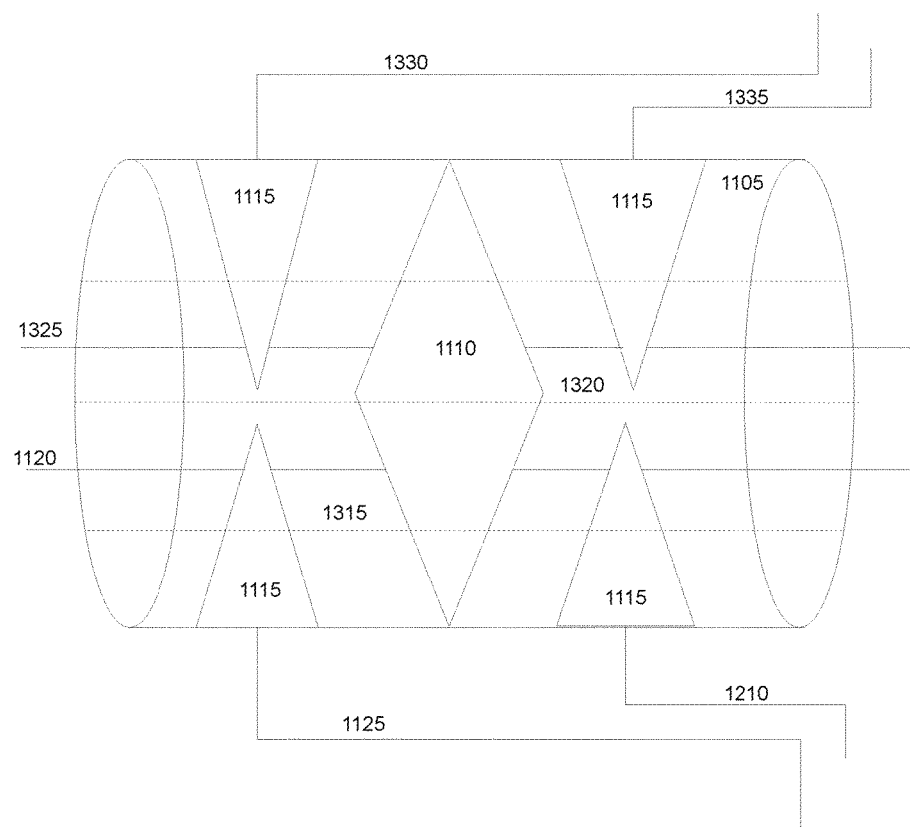
FIG. 13 illustrates aspects of a clamp for connecting a multifunction communication cube (MCC) to an electrical power circuit, in an embodiment.

As shown in FIGS. 11-13, a multifunction communication cube (MCC) may be connected or spliced into an electrical circuit without interrupting the downstream power flow of the circuit through use of a specially designed clamp. Referring to FIG. 11, clamp 1100 may be an insulated tube 1105 that has a single, non-conductive (glass, ceramic, etc.) blade 1110. In some embodiments, clamp 1100 may include a conductive blade 1115 that may be narrower at the top than at the bottom, and made of a conductive material (copper at minimum) and a contact pad 1130 connected to the top of the conductive blade via solder, wire etc. The contact pad 1130 allows for current to flow from the inside of the insulated tube 1105 to the outside of the insulated tube 1105. The contact pads 1130 have a wire connector 1125 that may transfer power from the insulated tube 1105 to an external device (not shown). It will be understood that this design accommodates a single wire 1120 conductor. FIG. 12 illustrates clamp 1200 in an alternative embodiment for tapping a single wire 1120 conductor. Clamp 1200 may accommodate one wire and may include two conductive blades 1115, positioned on opposite sides of the non-conductive blade 1110. Each of the two conductive blades 1115 may be attached to exiting wires 1125, and 1210, which may carry signals from each end of the severed wire 1120. In embodiments, such a clamp may splice the MCC into a conductor of a circuit while simultaneously transmitting current to devices on the circuit downstream of the CC.

To facilitate this non-interrupting splicing the power line wire may be laid inside of the insulated tube 1105. Once the wire 1120 is inside of the insulated tube 1105, the insulated tube 1105 is closed driving the non-conductive blade 1110 through the wire 1120 severing the connection between the upstream power source (upstream) and downstream powered device (downstream), and driving the conductive blades 1115 on either side of the non-conductive blade 1110 through the wire's insulation, causing the conductive blades 1115 to make electrical contact with the wire 1120 simultaneously. Contact being made with the wire 1120 and severing said wire 1120 will cause power to redirect through the conductive blades 1115. Power re-directed to the pads may be transferred from the pads on the outside of the tube to a wiring harness. This allows power to be diverted through the wire harness from the upstream side of the conductive blades to an external device (in this instance to CC). Once the MCC and clamp are connected to the power line, the power signal is processed, analyzed, manipulated etc. in the CC. Power may then be transmitted from the MCC through the clamp, through the wire harness connected to the downstream side and through the contact pad. Additionally, the MCC may provide signals via the power line by passing power signals and/or additional signals from the MCC through the contact pads to the conductive blades. The signals are then passed from the conductive blade to the downstream section of the wire in contact therewith. The power signals then pass along the wire to the device being powered, thus completing a single leg of the circuit. In the instance of a single wire clamp the process needs to be repeated for other the leg of the circuit.

Referring to FIG. 13, for a double-wire embodiment, in which the clamp 1300 allows for splicing into a circuit having a positive and a negative wire, the tube 1105 is designed to have two channels 1315, 1320. Each of the two wires 1325, 1120 are laid inside of the tube 1105, one wire in each channel. The tube 1105 is closed driving the non-conductive blade 1110 through each of the wires 1120, 1325 severing their connection between the upstream power source (upstream) and downstream powered device (downstream), and driving the conductive blades 1115 on either side of the non-conductive blade 1110 through the wire's insulation causing the conductive blades 1115 to make electrical contact with the conductor of each wire 1120, 1325 simultaneously. The tube 1105 closing will drive the conductive blades 1115 through the insulation around the respective wires 1120, 1325 in each channel 1315, 1320 until the conductive blades 1115 make contact with the conductive portions of the wires 1120, 1325. Contact being made with the wire 1120, 1325 and severing the wire 1325, 1120 will cause power to redirect through the conductive blades 1115. It is important to note that there should be a separate set of conductive blades for each wire into which the clamp is being used to splice. The separate sets of conductive blades allow for re-direction of the signals from each wire through the associated set of conductive blades without shorting out any connection. Power re-directed to the pads may be transferred from the pads on the outside of the tube to output wires 1125, 1210, 1330, 1335. This allows power to be diverted through the wire harness from the upstream side of the conductive blades to an external device (in this instance to CC). Once the MCC and clamp is connected to the power line power is processed, analyzed, manipulated etc. in the CC. Power may then be transmitted from the MCC through the clamp, through the wire harness connected to the downstream side and through the contact pad. Additionally, the MCC may provide signals via the power line by passing power/signals from the MCC through the contact pads to the conductive blades. The signals are then passed from the conductive blade to the downstream section of the wire they are making contact with. The power then passes along the wire to the device being powered, thus completing a single leg of the circuit. In the instance of a single wire clamp the process needs to be repeated for other the leg of the circuit. In the instance of a double wire clamp the process is closed due to both positive and negative wire running through the same clamp.

In embodiments, the clamp may be configured for any number of wires. For such embodiments, the clamp may comprise a number of wire channels equal to the number of wire into which the clamp is to splice. The clamp should additionally comprise a separate set of conductive blades for severing and re-directing the signal from each wire. The conductive blades should be separated such that no short circuiting of any of the wires occurs due to electrical contact between one conductive blade and multiple wires. A single non-conductive blade may be used to sever any number of wires as it is non-conductive and thus will not cause any short circuiting.

In embodiments, the conductive blades may comprise a V-shape.

Figure 6:
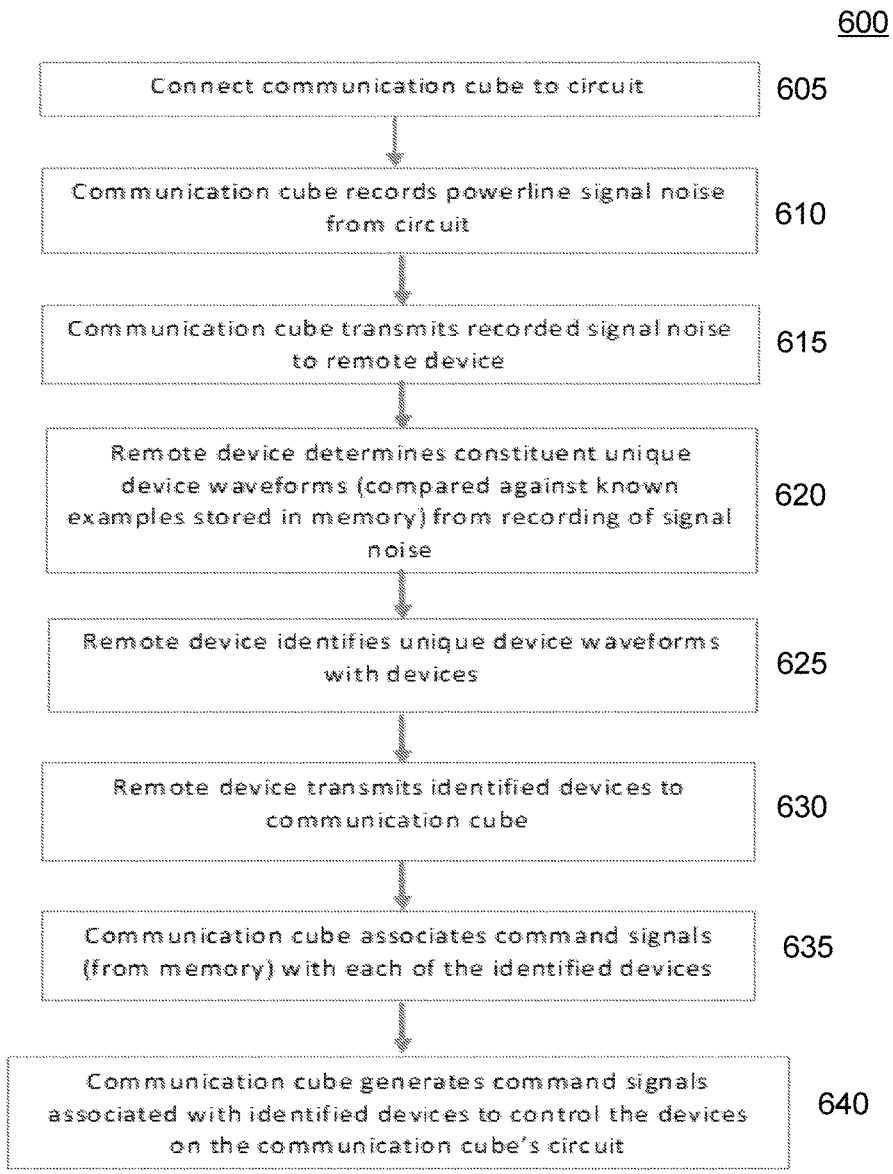
FIG. 6 illustrates a method for communicating with, identifying, monitoring and controlling electronic devices connected to a circuit, in an embodiment.

Referring to FIG. 6, in an embodiment disclosed subject matter includes method 600 for identification, communication, monitoring, and control of electronic devices connected to a circuit. Method 600 may include connecting 605 a multifunction communication cube (CC) to the circuit. It will be understood that the multifunction communication cube (CC) may have a construction, features and functionality as described elsewhere in this application. A subject circuit may be, for example, an electrical circuit of a building to provide power to electronic devices, or any other suitable circuit. The MCC may be connected to at least one conductor of the subject circuit via a clamp as described hereinabove, or may be otherwise connected or installed in conductive relationship with at least one conductor or wire of the subject circuit. Method 600 may include recording 610 signal noise from the circuit by the multifunction communication cube (CC) to provide recorded signal noise. Method 600 may include transmitting 615 the recorded signal noise to a remote device, such as a remote server, via a connection to an external communications network. It will be understood that, for example, the remote server may be accessed over the Internet. Method 600 may include determining 620 constituent unique device waveforms in the recorded signal noise, by the remote device or server, such as by a processor of the remote server comparing the recorded signal noise with samples of known unique device waveforms of known devices from a database. It will be understood that one suitable database of known devices and device waveforms may be, for example, the MIT Project Dilon signal fingerprint database. Method 600 may include identifying 625 devices connected to the subject circuit by identifying unique device waveforms of known devices that produce same from the database, by the remote server. Method 600 may include transmitting 630 identifications of devices to the communications cube (CC) from the remote server over a suitable communications network. Method 600 may include associating 635 command signals with each identified device connected to the subject circuit by a processor of the communications cube (CC). It will be understood that command signals of devices may be obtained from local memory of the communications cube (CC). Method 600 may include generating 640 command signals associated with identified devices by the processor of the communications cube (CC) on the subject circuit, to interact with and control aspects of such identified devices. It will be understood that, in an embodiment, command signals may also be communicated to identified devices over an output other than the subject circuit, such as over a wireless connection to an identified device, via a suitable wireless subsystem of the communications cube (CC). It will be understood that method 600 may be performed by any suitable system such as, for example, system 900 shown in FIG. 9.

Figure 7:
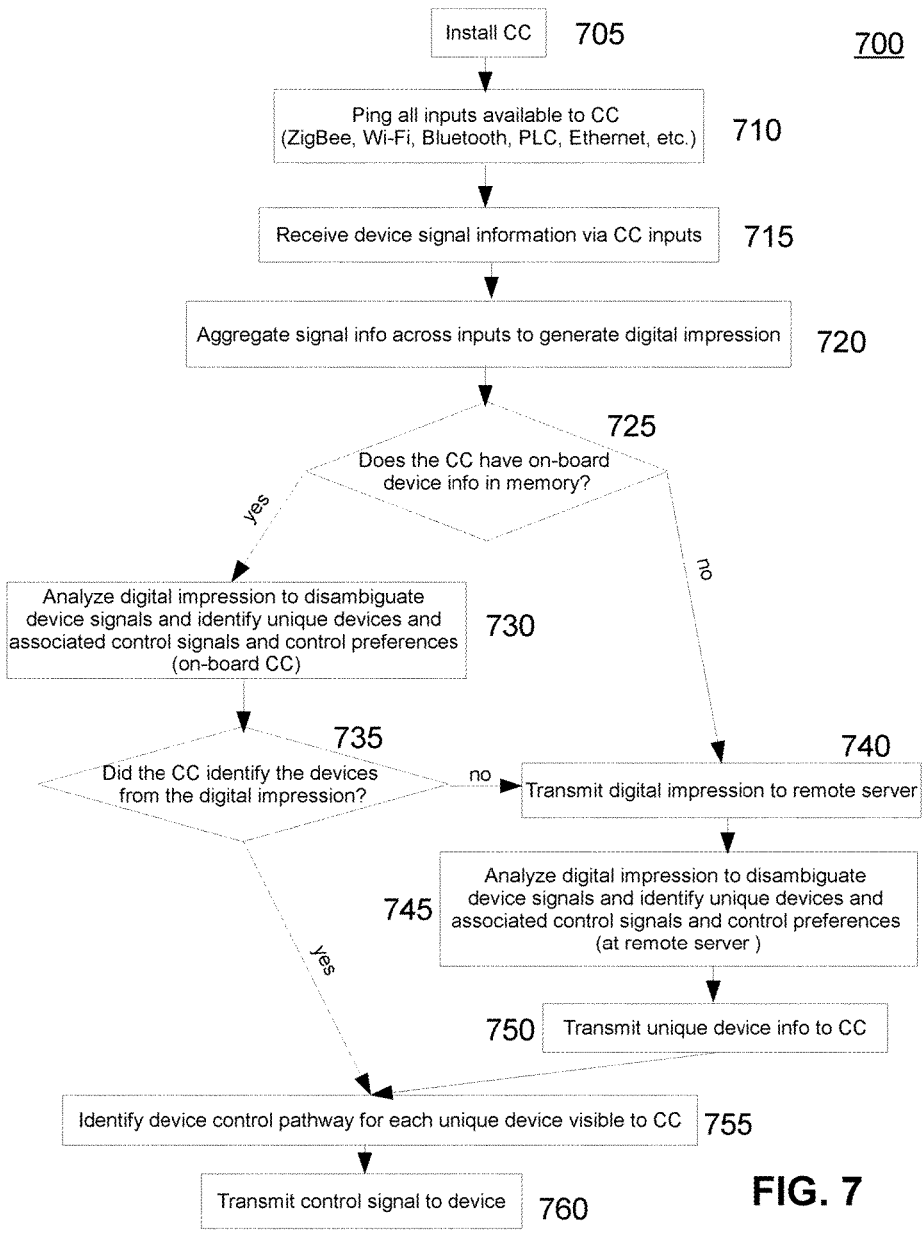
FIG. 7 illustrates a method for communicating with, identifying, monitoring and controlling electronic devices connected to a circuit, in an embodiment.

Referring to FIG. 7, in an embodiment disclosed subject matter includes method 700 for identification, communication, monitoring, and control of electronic devices at a site. Method 700 may include installing 705 a multifunction communication cube (CC) at the site. It will be understood that each multifunction communication cube (CC) may have a construction, features and functionality as described elsewhere in this application. A site may include, for example, at least one subject wired circuit, at least one subject wireless communication channel, or both, connected to at least one subject electronic device. A subject circuit may be, for example, an electrical circuit of a building to provide power to electronic devices, or any other suitable circuit such as a wired Ethernet connection of such a building. The MCC may be connected to at least one conductor of the subject circuit via a clamp as described hereinabove, or may be otherwise connected or installed in conductive relationship with at least one conductor or wire of the subject circuit. A subject wireless communication channel may be, for example, a ZigBee, Wi-Fi or Bluetooth wireless communication channel or infrastructure associated with the building or structure at the site, associated with a network at the site, or associated with subject wireless electronic devices present at the site. Method 700 may include pinging 710 over all available inputs of the MCC to respective subject circuits and subject wireless communications channels. Method 700 may include receiving 715 device signal information, signal noise, and/or conflated device signals via available inputs of the MCC from the respective subject circuits and subject wireless communications channels. Method 700 may include aggregating 720 by the MCC device signal information, signal noise and/or conflated device signals recorded from each of the inputs of the CC, to generate an aggregated digital impression or multidimensional digital impression information including recorded signal noise and recorded wireless communications information. Method 700 may include MCC disambiguation determining or analyzing 725 constituent unique device waveforms in recorded device signal information, signal noise and/or conflated device signals, by a local processor of the MCC comparing the recorded device signal information, signal noise and/or conflated device signals with samples of known unique device waveforms of known devices and/or devices previously or contemporaneously identified at the site, which are stored in MCC memory and/or stored in a local database of the MCC or any MCC in communication with the subject MCC at the site. Method 700 may include local identifying 735 of devices from the aggregated digital impression information by the CC. Method 700 may include transmitting 740 aggregated digital impression information from the MCC to a remote device, such as a remote server, via a connection to an external communications network. It will be understood that, for example, the remote server may be accessed over the Internet. Method 700 may include remote disambiguation determining or analyzing 745 aggregated digital impression or multidimensional digital impression information including recorded signal noise and recorded wireless communications information to identify constituent unique device waveforms in recorded device signal information, signal noise and/or conflated device signals, and to identify constituent device wireless communications properties or wireless constituent device identification information, by a remote processor of the remote server comparing the recorded device signal information, signal noise and/or conflated device signals with samples of known unique device waveforms of known devices and/or devices previously or contemporaneously identified at the site, and comparing recorded wireless communications information with known wireless communications information or properties of known devices or device types to identify constituent device wireless communications properties or wireless constituent device unique identification information, which are stored in memory associated with the remote server and/or stored in a remote database. It will be understood that one suitable database of known devices and device waveforms and identification information may be, for example, the MIT Project Dilon signal fingerprint database. Analyzing 745 may include identifying devices connected to a subject circuit or capable of communicating over a subject wireless communication channel or wireless infrastructure at the site, by identifying unique device waveforms of known devices that produce same, or identifying device wireless communications information or properties of known device, from the database, by the remote server. Method 700 may include transmitting 750 identifications of devices to the communications cube (CC) from the remote server over a suitable communications network. Method 700 may include associating 755 device control pathways, such as command signals, with each identified device connected to a subject circuit connected to the MCC or visible over a wireless communications connection or channel to the CC, by a processor of the communications cube (CC). It will be understood that command signals of devices may be obtained from local memory of the communications cube (CC). Method 700 may include generating or transmitting 760 command signals or control associated with identified devices by the processor of the communications cube (CC) on the subject circuit, and/or over a wireless communications connection or channel, to interact with and control aspects of such identified devices. It will be understood that, in some embodiments, command signals or control signals may be communicated to such identified devices over a wireless connection to an identified device, via a suitable wireless subsystem of the communications cube (CC). It will be understood that method 700 may be performed by any suitable system such as, for example, system 900 shown in FIG. 9.

Figure 8:
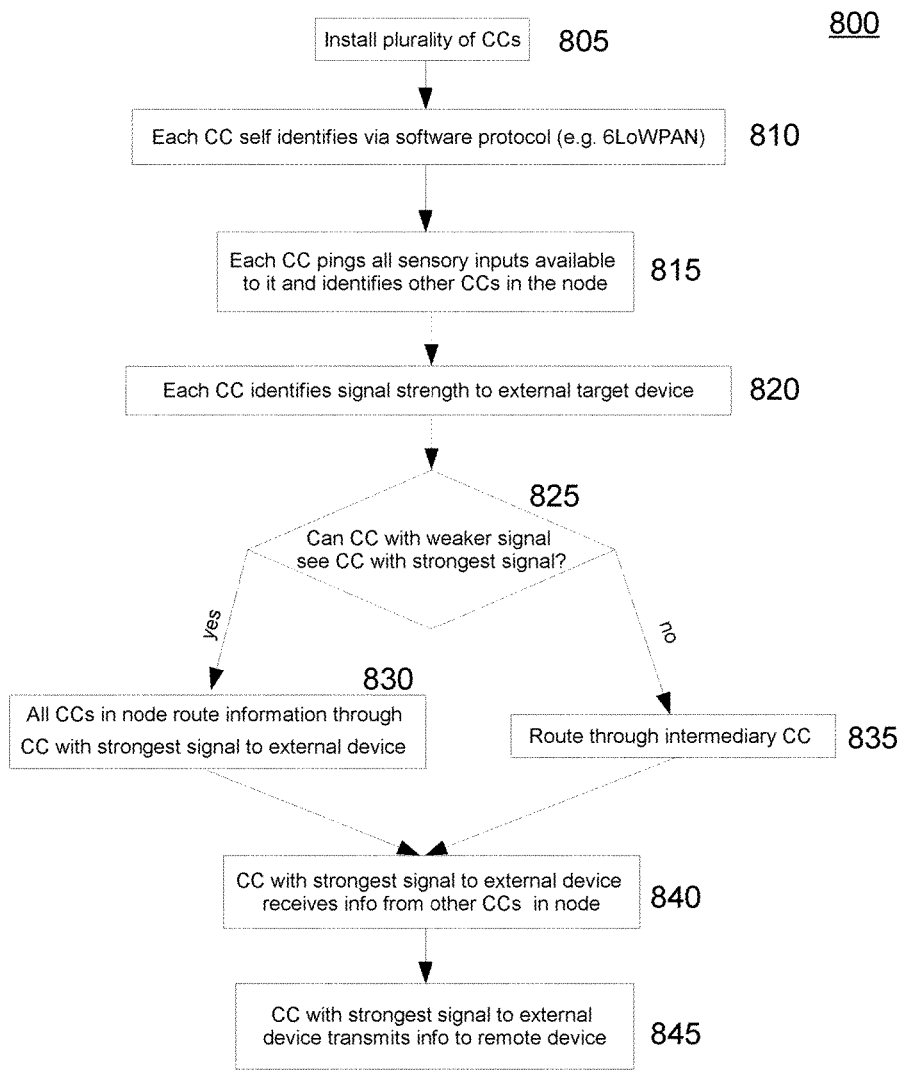
FIG. 8 illustrates a method for communicating with, identifying, monitoring and controlling electronic devices connected to a circuit, in an embodiment.

Referring to FIG. 8, in an embodiment disclosed subject matter includes method 800 for identification, communication, monitoring, and control of electronic devices at a site or node. Method 800 may include installing 805 a plurality of multifunction communication cubes (CC's) at the site or node. It will be understood that each multifunction communication cube (CC) may have a construction, features and functionality as described elsewhere in this application. A site may include, for example, at least one subject wired circuit, at least one subject wireless communication channel, or both, connected to at least one subject electronic device. Method 800 may include self-identifying 810 by each MCC via a self-identification protocol. A suitable self-identification protocol may be embodied in processor accessible code, such as software code. In an embodiment, a suitable self-identification protocol is 6LowPan. Method 800 may include pinging 815 by each MCC all sensory inputs, including available communications inputs, to identify all other CC's in the node. Method 800 may include identifying 820 by each MCC signal strength to an external target device such as, for example, a wireless network access point or wireless communications transceiver, for communication to a remote server over an external communications network such as, for example, the Internet. It will be understood that a suitable wireless communications transceiver may include a transceiver of a wireless mobile data network or cellular communications network. Method 800 may include identifying 820 signal strengths from each MCC to an external target device. Method 800 may include determining 825 whether each MCC having a relatively weaker signal strength to an external target device can see and enter into communications with another MCC having relatively strongest signal strength to an external target device. Method 800 may include direct routing 830 of information by all CC's in the node through a MCC identified as having the relatively strongest signal strength to an external target device. Method 800 may include indirect routing 835 of information by any CC's in the node to an intermediary MCC and from the intermediary MCC through a MCC identified as having the relatively strongest signal strength to an external target device. Method 800 may include receiving 840 information by a MCC identified as having the relatively strongest signal strength to an external target device, from other CC's in the node. Method 800 may include transmitting 845 information by the MCC identified as having the relatively strongest signal strength to an external target device, to said external target device. It will be understood that the particular MCC identified as having relatively strongest signal strength to an external target device may change from time to time as conditions at the site change, or as external target devices such as external wireless infrastructure changes. It will be understood that method 800 may be performed by any suitable system such as, for example, system 900 shown in FIG. 9.

Figure 9:
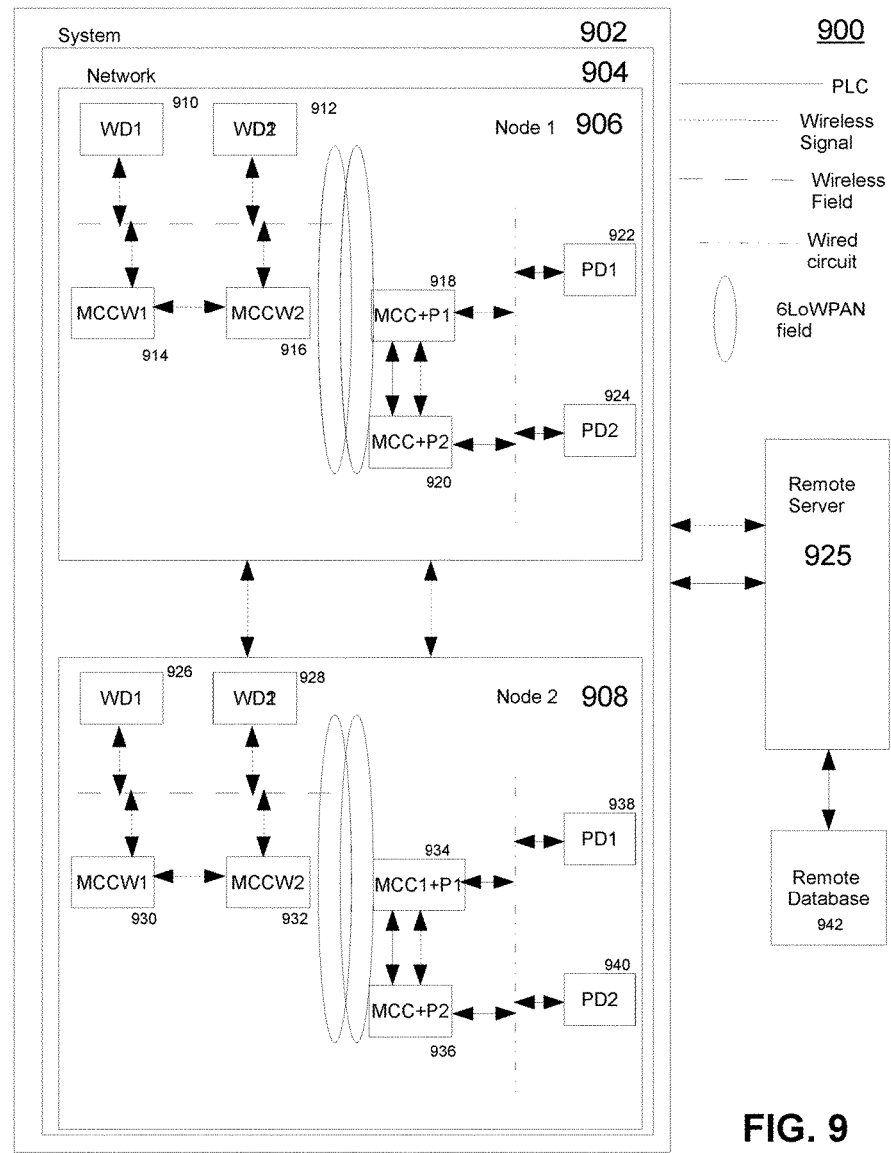
FIG. 9 illustrates a system for communicating with, identifying, monitoring and controlling electronic devices connected to a circuit, in an embodiment.

Referring to FIG. 9, in an embodiment disclosed subject matter includes system 900 for identification, communication, monitoring, and control of electronic devices at a site. System 900 may include a first node 906 and second node 908 at the site. The first node 906 and second node 908 may be identical, except that each node may be connected to different infrastructure at the site and/or each node may include different sets or groups of multifunction communication cubes (MCC's). The first node 906 is exemplary and will be described in further detail. First node 906 may include a plurality of multifunction communication cubes (MCC's) (914, 916, 918, 920) at the site. It will be understood that each multifunction communication cube (914, 916, 918, 920) may include all, or a subset, of the same or similar components, features, and functionality of apparatus 100, apparatus 200, and apparatus 300 described in detail elsewhere in this application. In the particular embodiment shown in FIG. 9, the multifunction communication cubes (MCC's) are more specifically characterized by reference to such devices including wireless communications subsystems (MCCW1, MCCW2), and other such devices including both wireless communications subsystems and wired or powerline connections (designated MCCW+P1, MCCW+P2). First node 906 may include, for example, multifunction communication cubes (MCC's designated MCCW+P1, MCCW+P2) connected to a subject wired circuit having at least one subject wired device (PDI, PD2) connected thereto. A subject circuit may be, for example, an electrical circuit of a building to provide power to electronic devices, or any other suitable circuit such as a wired Ethernet connection of such a building. As shown in FIG. 9, each MCC may be connected to at least one conductor of the subject circuit via a clamp as described elsewhere and shown in FIGS. 11-13, or may be otherwise connected or installed in conductive relationship with at least one conductor or wire of the subject circuit. First node 906 may include, for example, multifunction communication cubes (MCC's designated MCCW1, MCCW2, MCCW+P1, MCCW+P2) each connected to subject wireless communication channels and providing wireless connections to each subject wireless electronic device (WDI, WD2) within wireless reception and transmission range of such multifunction communication cubes (MCC's designated MCCW1, MCCW2, MCCW+P1, MCCW+P2). A subject wireless communication channel may be, for example, a ZigBee, Wi-Fi or Bluetooth wireless communication channel or infrastructure associated with the building or structure at the site, associated with a network at the site, or associated with subject wireless electronic devices present at the site. Each MCC may ping over all available inputs (P1, P2) of the MCC to a subject wired circuit to subject wired devices (PDI, PD2) and to subject wireless communications channels to subject wireless devices (WDI, WD2). The plurality of multifunction communication cubes (MCC's designated MCCW1, MCCW2, MCCW+P1, MCCW+P2) each may also include suitable wireless communication subsystems, such as 6LoWPAN subsystems, providing wireless communication channels and enabling wireless connections with each other multifunction communication cube (MCC's designated MCCW1, MCCW2, MCCW+P1, MCCW+P2) within wireless reception and transmission range of such multifunction communication cubes (MCC's designated MCCW1, MCCW2, MCCW+P1, MCCW+P2). Each of the multifunction communication cubes (MCC's designated MCCW1, MCCW2, MCCW+P1, MCCW+P2) may receive device signal information, signal noise, and/or conflated device signals via available inputs of the MCC from the respective subject circuits and subject wireless communications channels. Each of the multifunction communication cubes (MCC's designated MCCW1, MCCW2, MCCW+P1, MCCW+P2) may aggregate by an MCC local processor device signal information, signal noise and/or conflated device signals recorded from each of the inputs of the CC, to generate an aggregated digital impression or multidimensional digital impression information including recorded signal noise and recorded wireless communications information. Each of the multifunction communication cubes (MCC's designated MCCW1, MCCW2, MCCW+P1, MCCW+P2) may perform disambiguation determining or analyzing of constituent unique device waveforms in recorded device signal information, signal noise and/or conflated device signals, by the local processor of the MCC comparing the recorded device signal information, signal noise and/or conflated device signals with samples of known unique device waveforms of known devices and/or devices previously or contemporaneously identified at the site, which are stored in MCC memory and/or stored in a local database of the MCC or any MCC in communication with the subject MCC at the site. Each of the multifunction communication cubes (MCC's designated MCCW1, MCCW2, MCCW+P1, MCCW+P2) may perform local identifying of devices from the aggregated digital impression information by the MCC. Each of the multifunction communication cubes (MCC's designated MCCW1, MCCW2, MCCW+P1, MCCW+P2) may perform transmitting of aggregated digital impression information from the MCC to a remote device, such as a remote server 925, via a connection to an external communications network. It will be understood that, for example, the remote server 925 may be accessed over the Internet. Remote server 925 may perform remote disambiguation determining or analyzing of aggregated digital impression or multidimensional digital impression information including recorded signal noise and recorded wireless communications information to identify constituent unique device waveforms in recorded device signal information, signal noise and/or conflated device signals, and to identify constituent device wireless communications properties or wireless constituent device identification information, by a remote processor of the remote server 925 comparing the recorded device signal information, signal noise and/or conflated device signals with samples of known unique device waveforms of known devices and/or devices previously or contemporaneously identified at the site, and comparing recorded wireless communications information with known wireless communications information or properties of known devices or device types to identify constituent device wireless communications properties or wireless constituent device unique identification information, which are stored in memory (not shown) associated with the remote server and/or stored in a remote database (not shown). It will be understood that one suitable database of known devices and device waveforms and identification information may be, for example, the MIT Project Dilon signal fingerprint database. Remote server 925 may perform analyzing to identify devices connected to a subject circuit or capable of communicating over a subject wireless communication channel or wireless infrastructure at the site, by identifying unique device waveforms of known devices that produce same, or identifying device wireless communications information or properties of known devices, from the remote database. Remote server 925 may transmit identification information of devices from the remote server over a suitable communications network to the multifunction communication cubes (MCC's designated MCCW1, MCCW2, MCCW+P1, MCCW+P2). Each of the multifunction communication cubes (MCC's designated MCCW1, MCCW2, MCCW+P1, MCCW+P2) may perform associating of device control pathways, such as command signals, with each identified device connected to a subject circuit connected to a multifunction communication cube (MCC's designated MCCW1, MCCW2, MCCW+P1, MCCW+P2) or visible over a wireless communications connection or channel to a multifunction communication cubes (MCC's designated MCCW1, MCCW2, MCCW+P1, MCCW+P2), by a processor of the same. It will be understood that command signals of devices may be obtained from local memory of the multifunction communication cubes (MCC's designated MCCW1, MCCW2, MCCW+P1, MCCW+P2). Multifunction communication cubes (MCC's designated MCCW1, MCCW2, MCCW+P1, MCCW+P2) by the local MCC processor may generate or transmit command signals or control signals associated with identified devices connected to the subject circuit, and/or over a wireless communications connection or channel, to interact with and control aspects of such identified devices. It will be understood that, in some embodiments, command signals or control signals may be communicated to such identified devices over a wireless connection to an identified device, via a suitable wireless subsystem of the multifunction communication cubes (MCC's designated MCCW1, MCCW2, MCCW+P1, MCCW+P2). It will be understood that the first node 906 and second node 908 may communicate and share information regarding wired electronic devices (PD1, PD2) and wireless devices (WD1, WD2).

Figure 10:
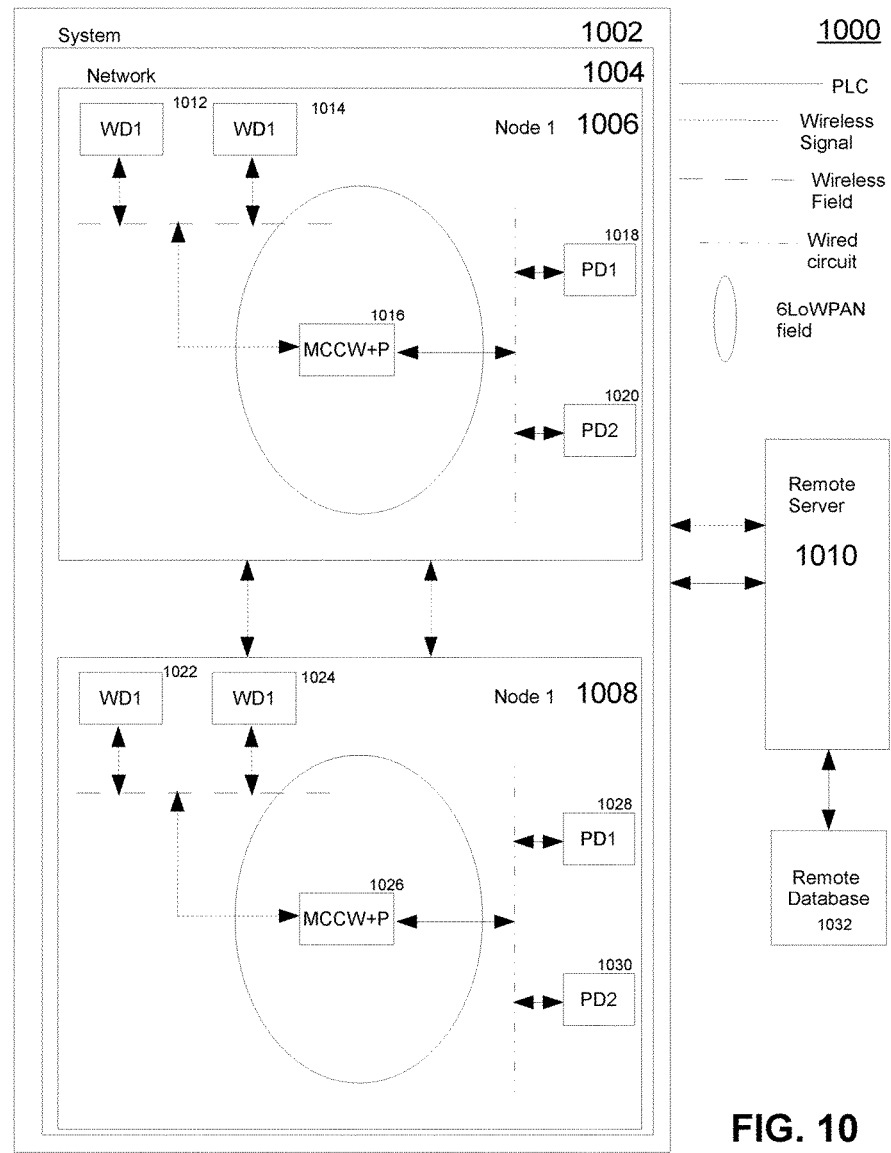
FIG. 10 illustrates a system for communicating with, identifying, monitoring and controlling electronic devices connected to a circuit, in an embodiment.

FIG. 10 illustrates a system 1000 including network 1004 having a first node 1006 and second node 1008. Each of the first node 1006 and second node 1008 include a respective single multifunction communication cube (MCC) (1016, 1026) having wireless and wired communications capabilities and subsystems. System 1000 may be otherwise identical, or substantially similar, to system 900 illustrated in FIG. 9.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

The benefits and advantages that may be provided by the present invention have been described above with regard to specific embodiments. These benefits and advantages, and any elements or limitations that may cause them to occur or to become more pronounced are not to be construed as critical, required, or essential features of any or all of the claims. As used herein, the terms "comprises," "comprising," or any other variations thereof, are intended to be interpreted as non-exclusively including the elements or limitations which follow those terms. Accordingly, a system, method, or other embodiment that comprises a set of elements is not limited to only those elements, and may include other elements not expressly listed or inherent to the claimed embodiment.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed within the following claims.

What is claimed is:

1. An apparatus for controlling electronic devices through a power line, comprising:
   a processor;
   a memory coupled to the processor; and
   a control clamp coupled to the processor, the control clamp being configured to splice into the power line to provide electrical power and signals from the power line to the processor while continuously providing power from the power line to the electronic devices, wherein the control clamp comprises:
   one or more non-conductive blades; and
   one or more conductive blades, wherein the conductive blades are coupled to the processor;
   wherein the conductive blades are configured to splice into the power line and redirect power from the power line through the apparatus and to the electronic devices, and wherein at least one of the non-conductive blades is configured to sever the power line and disrupt power through the power line while the conductive blades are configured to substantially simultaneously splice into the power line;
   wherein the memory stores program instructions executable by the processor to monitor and control at least one of the electronic devices through the control clamp.

2. The apparatus of claim 1, wherein the control clamp is configured to disrupt electrical power through the power line while simultaneously redirecting electrical power from the power line through the apparatus and to the electronic devices.

3. The apparatus of claim 1, further comprising a control port, the control port being configured to monitor electrical power signals associated with the electronic devices and send control signals to the electronic devices via one or more communication protocols.

4. The apparatus of claim 1, further comprising a power port, the power port being configured to receive power from the power line through the control clamp and provide power to the apparatus.

5. The apparatus of claim 1, wherein the memory stores program instructions executable by the processor to implement communicating with a remote device configured to control the apparatus.

6. The apparatus of claim 1, wherein the memory stores program instructions executable by the processor to implement assessing an identity of at least one of the electronic devices.

7. The apparatus of claim 1, further comprising a communication port, the communication port being configured to wirelessly communicate with a remote device.

8. The apparatus of claim 1, wherein the memory stores program instructions executable by the processor to implement assessing signal information for at least one of the electronic devices and assessing an aggregated digital impression of the at least one electronic device from the assessed signal information.

9. The apparatus of claim 1, wherein the conductive blades comprise at least a first conductive blade and a second conductive blade, the first conductive blade and the second conductive blade being offset from the non-conductive blade.

* * * * *